United States Patent
Mou et al.

(10) Patent No.: US 11,719,674 B2
(45) Date of Patent: Aug. 8, 2023

(54) MONITOR AND GAS DETECTION INFORMATION NOTIFICATION SYSTEM

(71) Applicant: MICROJET TECHNOLOGY CO., LTD., Hsinchu (TW)

(72) Inventors: Hao-Jan Mou, Hsinchu (TW);
Yung-Lung Han, Hsinchu (TW);
Chi-Feng Huang, Hsinchu (TW);
Chun-Yi Kuo, Hsinchu (TW);
Chang-Yen Tsai, Hsinchu (TW);
Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 386 days.

(21) Appl. No.: 16/998,021

(22) Filed: Aug. 20, 2020

(65) Prior Publication Data
US 2021/0063368 A1   Mar. 4, 2021

(30) Foreign Application Priority Data
Aug. 29, 2019 (TW) .................. 108131138

(51) Int. Cl.
*G01N 33/00* (2006.01)
(52) U.S. Cl.
CPC ..... *G01N 33/0034* (2013.01); *G01N 33/0008* (2013.01); *G01N 33/0062* (2013.01)
(58) Field of Classification Search
None
See application file for complete search history.

(56) References Cited

U.S. PATENT DOCUMENTS

| 6,114,964 | A  | * | 9/2000 | Fasano | G01N 33/0075 340/628 |
| 6,670,887 | B2 | * | 12/2003 | Dungan | G08B 21/16 340/632 |

(Continued)

FOREIGN PATENT DOCUMENTS

| CN | 105308657 A |   | 2/2016 |
| CN | 109425696 A |   | 3/2019 |
| TW | M574151 U | * | 2/2019 |

OTHER PUBLICATIONS

Machine translation of CN 105308657 published Feb. 3, 2016.
Machine translation of CN 109425696 published Mar. 5, 2019.

*Primary Examiner* — Daniel S Larkin
(74) *Attorney, Agent, or Firm* — McClure, Qualey & Rodack, LLP

(57) ABSTRACT

A monitoring and gas detection information notification system includes monitoring devices and a cloud data processing device. The monitoring devices are respectively disposed at corresponding fixed positions, each of the monitoring devices includes a monitoring module and an actuator-sensor module. The monitoring module captures an image and converts the image into an image data. The actuator-sensor module is disposed in the monitoring module and includes one or more actuators for guiding a gas into the monitoring module and includes one or more sensors for generating a gas detecting data. The cloud data processing device stores and intelligently analyzes the image data and the gas detecting data to generate a processed data, and the cloud data processing device transmits the processed data to a notification processing system so as to conduct a notification of monitoring information and gas detecting information.

18 Claims, 18 Drawing Sheets

(56) References Cited

U.S. PATENT DOCUMENTS

| | | | |
|---|---|---|---|
| 2016/0328612 A1* | 11/2016 | Ahn | G01N 33/004 |
| 2019/0032939 A1* | 1/2019 | Mou | F24F 11/0008 |
| 2019/0033177 A1* | 1/2019 | Mou | F04B 43/046 |
| 2019/0033278 A1* | 1/2019 | Mou | G08B 21/12 |
| 2019/0035249 A1* | 1/2019 | Mou | F24F 11/52 |
| 2019/0060943 A1* | 2/2019 | Mou | B05B 17/0607 |
| 2019/0170717 A1* | 6/2019 | Mou | G01N 33/0031 |

* cited by examiner

MONITOR AND GAS DETECTION INFORMATION NOTIFICATION SYSTEM

CROSS-REFERENCE TO RELATED APPLICATION

This non-provisional application claims priority under 35 U.S.C. § 119(a) to Patent Application No. 108131138 filed in Taiwan, R.O.C. on Aug. 29, 2019, the entire contents of which are hereby incorporated by reference.

BACKGROUND

Technical Field

The present disclosure relates to an environmental monitor application of an actuator-sensor module. In particular, to a monitoring and gas detection information notification system which combines an actuator-sensor module with a micro monitoring device, and further with a cloud data processing device that stores and intelligently analyzes data transmitted through a data network for further applications.

Related Art

At present, people pay more and more attention to monitoring ambient air quality in daily life, such as monitoring carbon monoxide, carbon dioxide, volatile organic compounds (VOC), PM2.5, etc. Exposure to these gases can cause adverse health effects on the human body, and can even be life-threatening. Therefore, monitoring ambient air quality has attracted the attention of various countries. How to implement the monitoring of ambient air quality becomes a topic that is to be paid attention to.

It is feasible to use sensors to monitor the ambient gas. If the detection information can be timely provided to warn people in a dangerous environment, so they can avoid or escape in time from the health affecting effects and/or injuries caused by the exposure to the ambient gas, then using the sensors to monitor the surrounding environment will be beneficial.

However, although using sensors to monitor the environment can provide users with more information about the environment, the performance of the monitoring sensitivity and accuracy needs to be further considered. For example, if the sensor solely relies on the inflow from the gas naturally flowing in the environment, not only a stable and consistent gas flow for steady monitoring cannot be obtained, but also the gas naturally flowing in the environment takes much more time to reach the sensor, thereby affecting the efficacy of real-time monitoring.

In addition, although there are large environmental monitoring base stations for monitoring ambient air quality at present, the construction equipment of these monitoring base stations is all large-scale equipment, so that it is impossible to popularize these monitoring base stations. Thus, the ambient air quality around the human cannot be effectively and accurately monitored. For example, the indoor air quality or the air quality near the user cannot be effectively and quickly monitored. Accordingly, if a sensor and an actuator can be combined with a micro monitoring device, then a real-time monitoring can be popularized, and moreover, the monitor information data can be transmitted to a cloud database for data construction and intelligent analysis in real time. Therefore, the application not only can provide a notification processing mechanism required for monitoring, but also can provide more accurate and real-time air quality monitoring information and maps for starting an air quality notification processing mechanism.

SUMMARY

One object of the present disclosure is providing a monitoring and gas detection information notification system which combines an actuator-sensor module with a micro monitoring device for a further application. By using a plurality of monitoring devices respectively disposed at different places, the air information of the places where the monitoring devices are respectively located can be monitored in real time. Therefore, a real-time monitoring of the air quality around the human can be achieved and can be easily popularized. Furthermore, by further establishing a data connection between a cloud data processing device and the monitoring devices through a data network, the system not only can provide a notification processing mechanism required for monitoring, but also can provide more accurate and real-time air quality monitoring information and maps for starting an air quality notification processing mechanism, which is an issue that needs to be solved.

To achieve the above mentioned purpose(s), a general embodiment of the present disclosure provides a monitoring and gas detection information notification system including a plurality of monitoring devices respectively disposed at corresponding fixed positions and a cloud data processing device. Each of the monitoring devices includes a monitoring module and an actuator-sensor module. The monitoring module captures an image of the corresponding fixed position, stores the image, converts the image into an image data, and outputs the image data. The actuator-sensor module is installed in the monitoring module and includes at least one actuator and at least one sensor. The at least one actuator guides gas outside the monitoring module into the monitoring module, and the at least one sensor detects the gas so as to generate a gas detecting data and output the gas detecting data. The cloud data processing device stores and intelligently analyzes the image data output by the monitoring module and the gas detecting data output by the actuator-sensor module. The image data and the gas detecting data are transmitted to the cloud data processing device by the monitoring module through a data network to generate a processed data, and the cloud data processing device transmits the processed data to a notification processing system so as to conduct a notification of monitoring information and gas detecting information.

BRIEF DESCRIPTION OF THE DRAWINGS

The disclosure will become more fully understood from the detailed description given herein below for illustration only, and thus not limitative of the disclosure, wherein.

DETAILED DESCRIPTION

The present disclosure will now be described more specifically with reference to the following embodiments. It is to be noted that the following descriptions of different embodiments of this disclosure are presented herein for purpose of illustration and description only, and it is not intended to limit the scope of the present disclosure.

Figure 1:
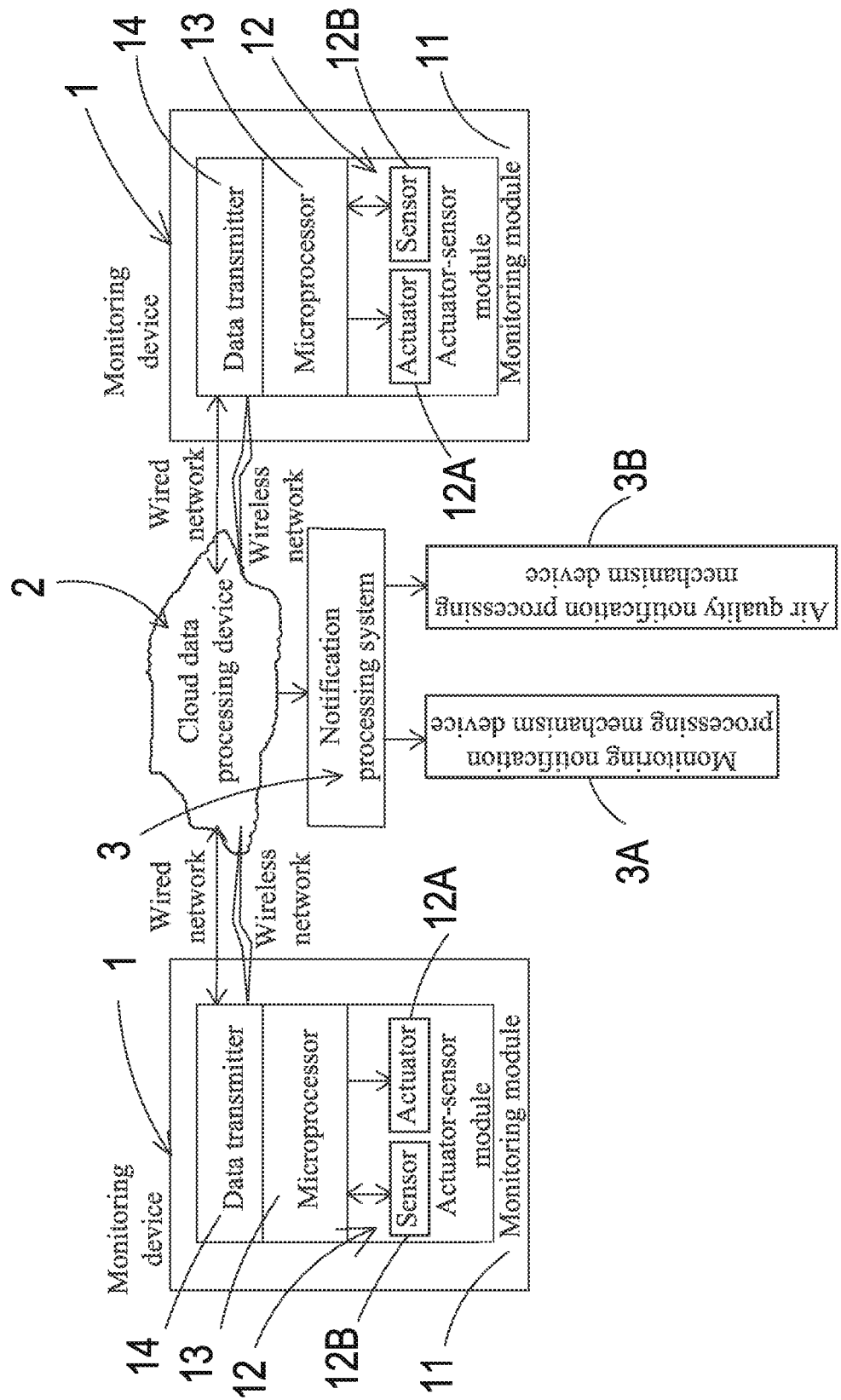
FIG. 1 illustrates a block diagram of a monitoring and gas detection information notification system according to an exemplary embodiment of the present disclosure.

Please refer to FIG. 1. The monitoring and gas detection information notification system of the present disclosure mainly includes a plurality of monitoring devices 1 and a cloud data processing device 2. The monitoring devices 1 are respectively disposed at different fixed positions for conducting monitoring, and each of the monitoring devices 1 establishes a data connection with the cloud data processing device 2. The cloud data processing device 2 stores and intelligently analyzes data output by the monitoring device 1 to generate a processed data, and the cloud data processing device 2 transmits the processed data to a notification processing system 3 so as to conduct a notification of monitoring information and a notification of gas detecting information.

Figure 8A:
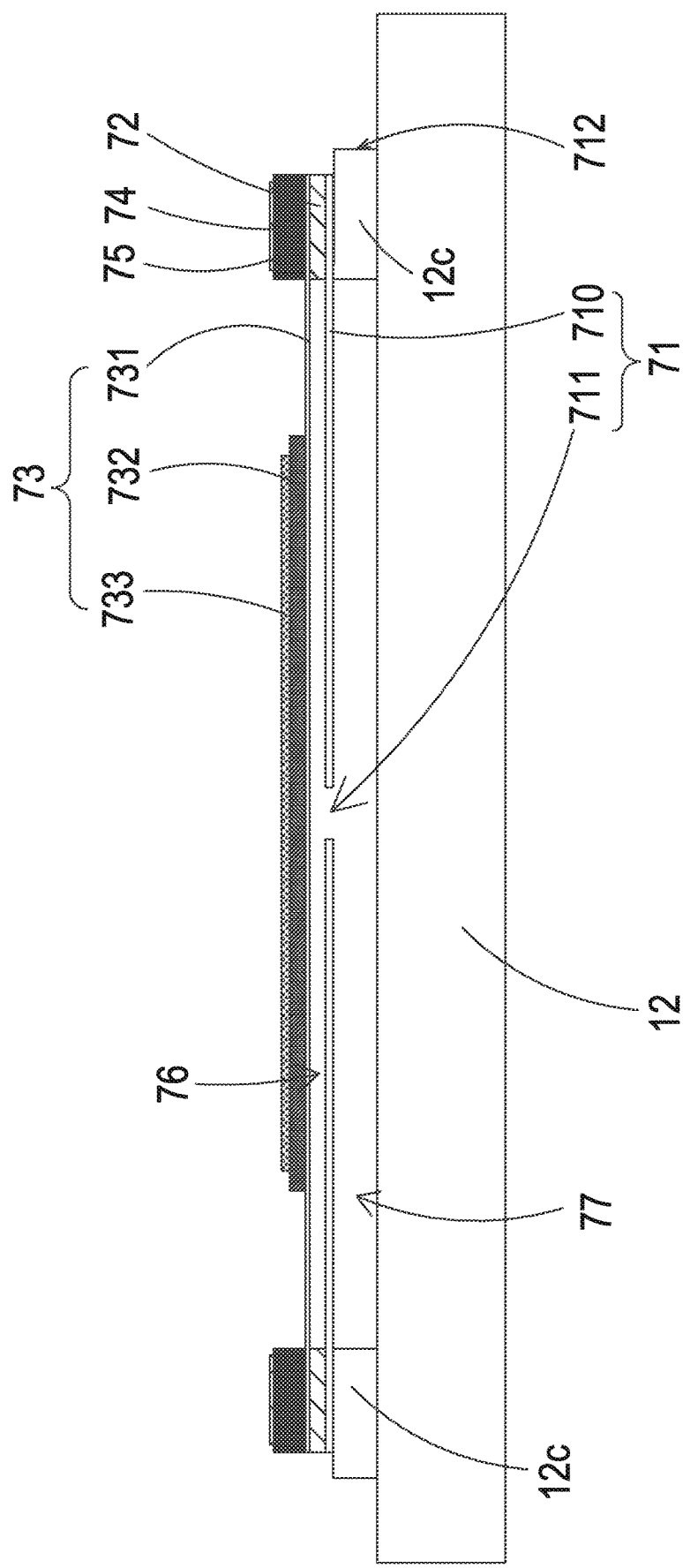
FIG. 8A illustrates a schematic cross-sectional view of the piezoelectric pump according to the second embodiment of the present disclosure.

The monitoring device 1 includes a monitoring module 11, an actuator-sensor module 12, a microprocessor 13, and a data transmitter 14. The monitoring module 11 captures an image of the corresponding fixed position, stores the image, converts the image into an image data, and outputs the image data. The actuator-sensor module 12 is installed in the monitoring module 11. In some embodiments, the actuator-sensor module 12 includes at least one actuator 12A, at least one sensor 12B, and four positioning bumps 12C (as shown in FIG. 8A). The actuator 12A guides a gas outside the monitoring module 11 into the monitoring module 11. The sensor 12B detects the gas so as to generate a gas detecting data and output the gas detecting data. The microprocessor 13 controls an operation of the monitoring module 11 and an operation of the actuator-sensor module 12, converts the image captured by the monitoring module 11 into the image data, and outputs the image data. Also, the microprocessor 13 converts a gas detecting value generated by the actuator-sensor module 12 into the gas detecting data and outputs the gas detecting data. The microprocessor 13 further transmits the image data and the gas detecting data to the data transmitter 14, and the image data and the gas detecting data is then transmitted to the cloud data processing device 2 through the data transmitter 14 for being stored and intelligently analyzed.

The sensor 12B may include any suitable sensor, such as a gas sensor, a microparticle sensor (e.g. a PM 2.5 microparticle sensor), a volatile organic compounds sensor (e.g. a formaldehyde sensor and an ammonia sensor), but is not limited thereto.

The sensor 12B is disposed at one side of the actuator 12A. The actuator 12A is driven to generate a gas flow toward the sensor 12B to provide a stable and consistent gas flow directly introduced to the sensor 12B. Therefore, the sensor 12B can obtain a stable and consistent gas flow, so that the sensor 12B can measure and/or detect the received gas directly, and the detection time of the sensor 12B can be reduced as well, thereby achieving an accurate and real-time monitoring.

Figure 3A:
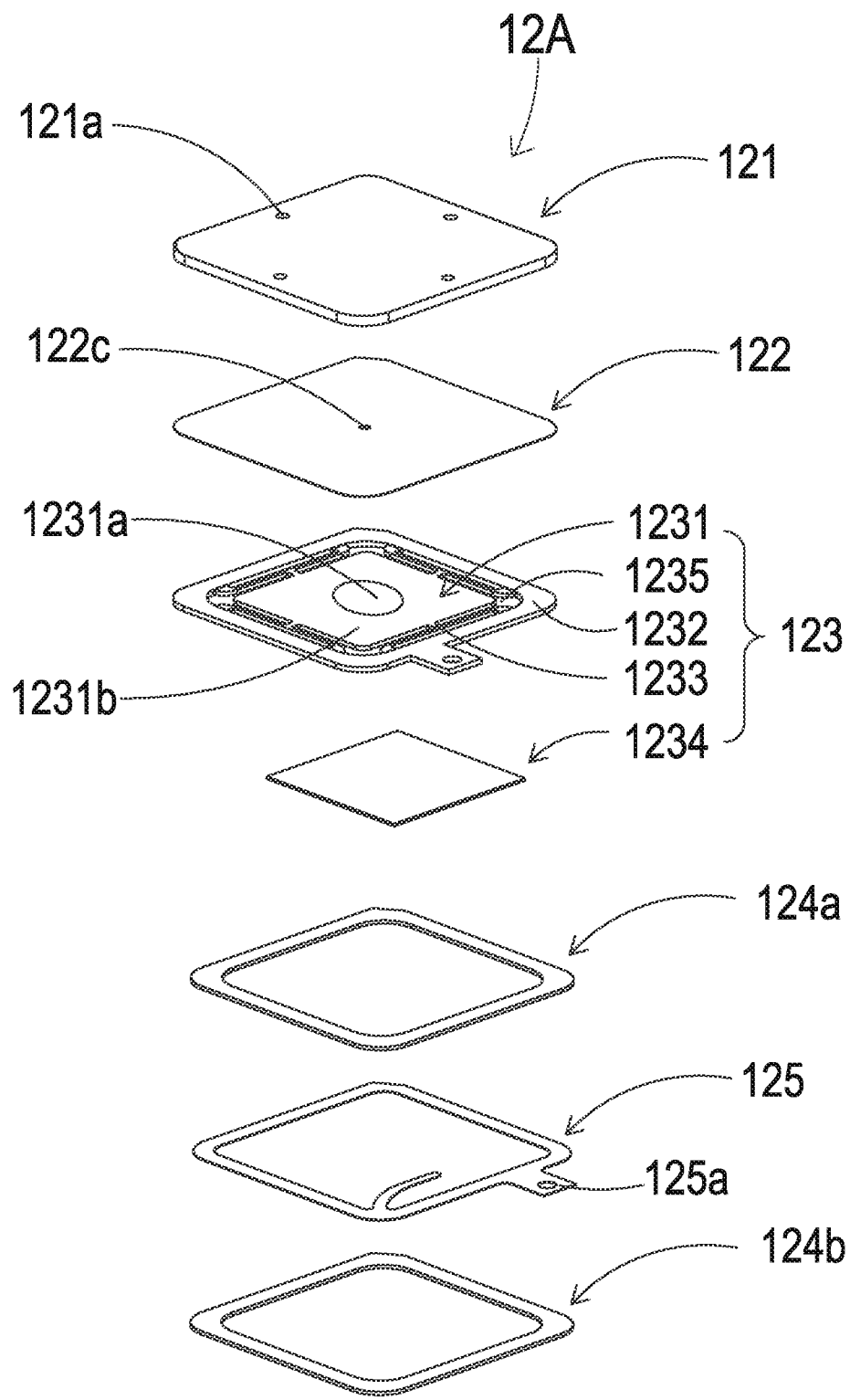
FIG. 3A and FIG. 3B respectively illustrate a front exploded view and a rear exploded view of a piezoelectric pump according to the first embodiment of the present disclosure.
Figure 3B:
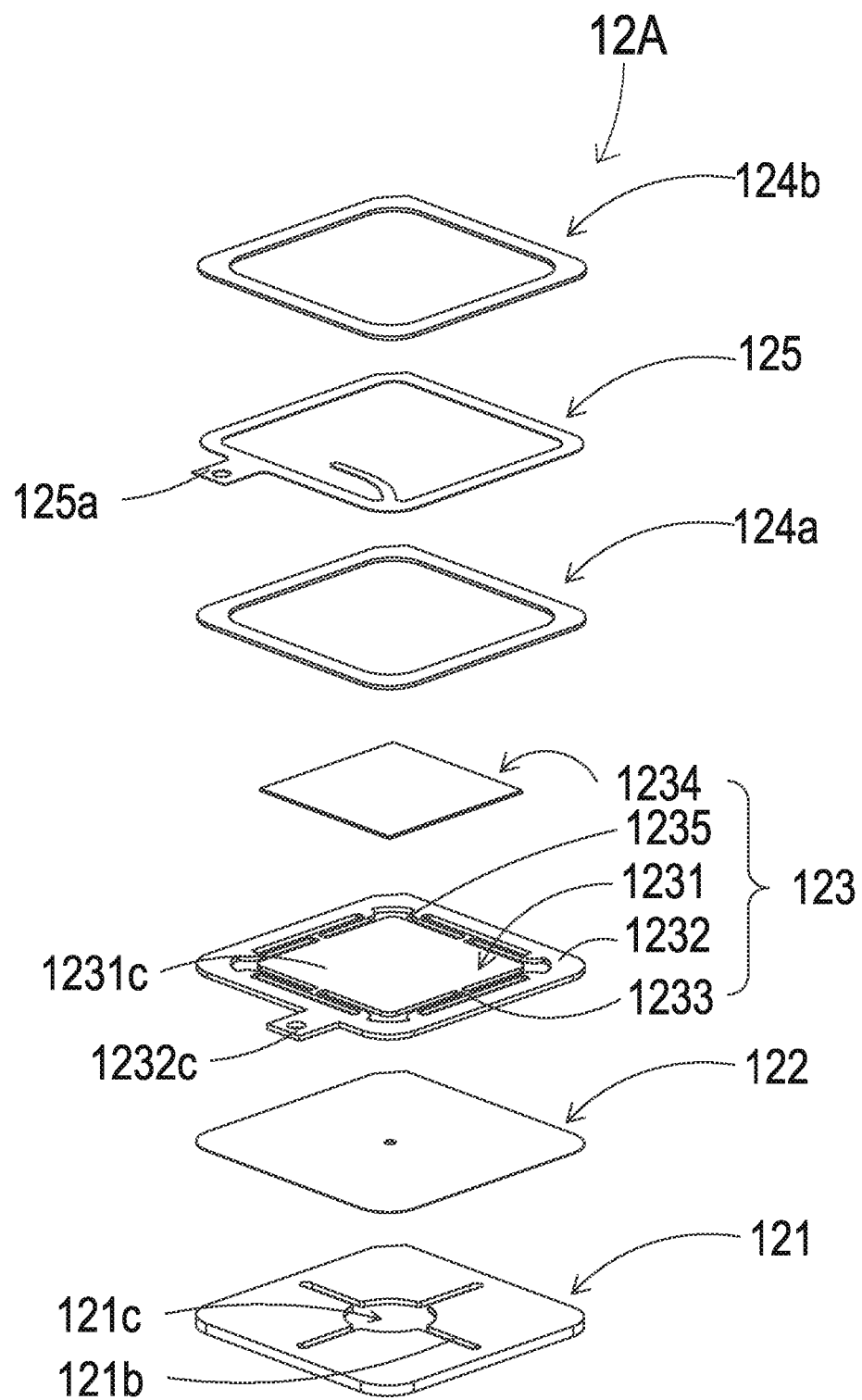

Please refer to FIG. 3A and FIG. 3B. In some embodiments, the actuator 12A may be a micro-electromechanical systems (MEMS) pump 8 or a piezoelectric pump. The following paragraphs describe the structure of the piezoelectric pump according to the first embodiment of the present disclosure.

Figure 5:
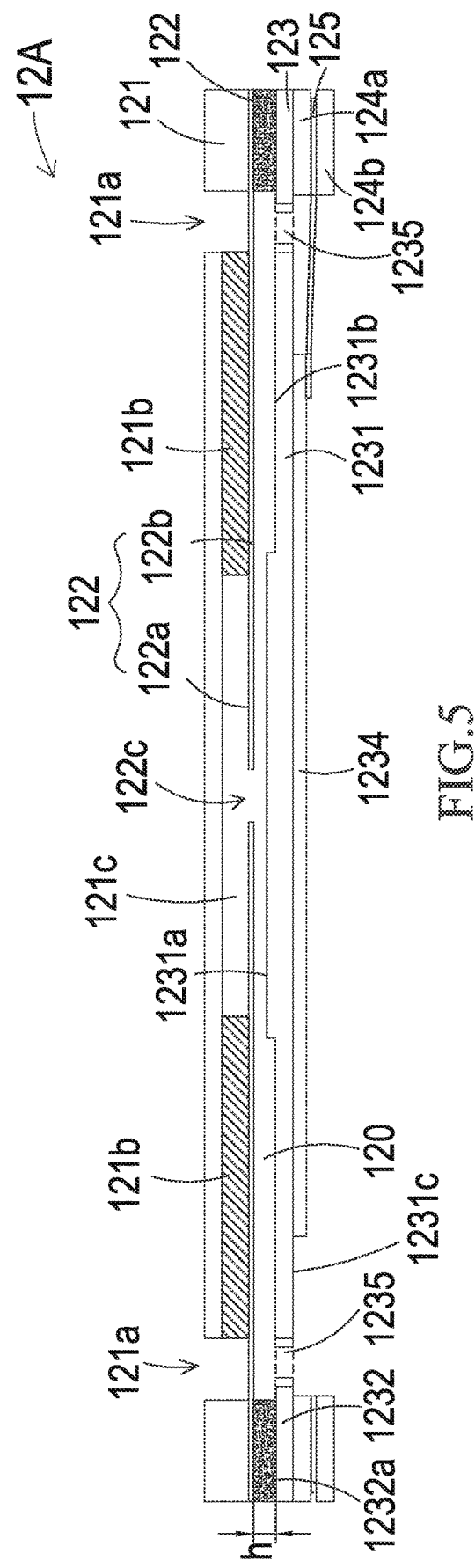
FIG. 5 illustrates a schematic cross-sectional view of the piezoelectric pump according to the first embodiment of the present disclosure.

The actuator 12A includes an inlet plate 121, a resonance sheet 122, a piezoelectric actuator 123, a first insulation sheet 124a, a conductive sheet 125, and a second insulation sheet 124b. The piezoelectric actuator 123 is disposed correspondingly to the resonance sheet 122. The inlet plate 121, the resonance sheet 122, the piezoelectric actuator 123, the first insulation sheet 124a, the conductive sheet 125, and the second insulation sheet 124b are sequentially stacked and assembled with each other. The cross-sectional view of the assembled structure of the actuator 12A is shown in FIG. 5.

In this embodiment, the inlet plate 121 has at least one inlet hole 121a. The number of the inlet hole 121a is preferably four, but not limited thereto. The inlet hole 121a is defined through the inlet plate 121, so that the gas outside the actuator 12A can flow into the actuator 12A from the at least one inlet hole 121a due to the atmospheric pressure effect. The inlet plate 121 has at least one convergence channel 121b, and the at least one convergence channel 121b corresponds to the at least one inlet hole 121a on the opposite side of the inlet plate 121. The convergence place of the convergence channels 121b has a central recess 121c, and the central recess 121c is in communication with the convergence channels 121b. Thus, the gas entering into the inlet plate 121 from the at least one inlet hole 121a can be guided and converged at the central recess 121c, thereby achieving gas transmission. In this embodiment, the inlet plate 121 is a one-piece element integrally formed with the inlet hole 121a, the convergence channel 121b, and the central recess 121c. The central recess 121c forms a convergence chamber for converging the gas so as to store the gas temporarily. In some embodiments, the inlet plate 121 is made of stainless steel, but is not limited thereto. In some other embodiments, the depth of the convergence chamber formed by the central recess 121c is substantially equal to the depth of the convergence channel 121b, but is not limited thereto. The resonance sheet 122 is made of a flexible material, but is not limited thereto. Moreover, the resonance sheet 122 has a perforation 122c corresponding to the central recess 121c of the inlet plate 121, whereby the gas in the convergence chamber can pass through the resonance sheet 122. In some other embodiments, the resonance sheet 122 is made of copper, but is not limited thereto.

Figure 4:
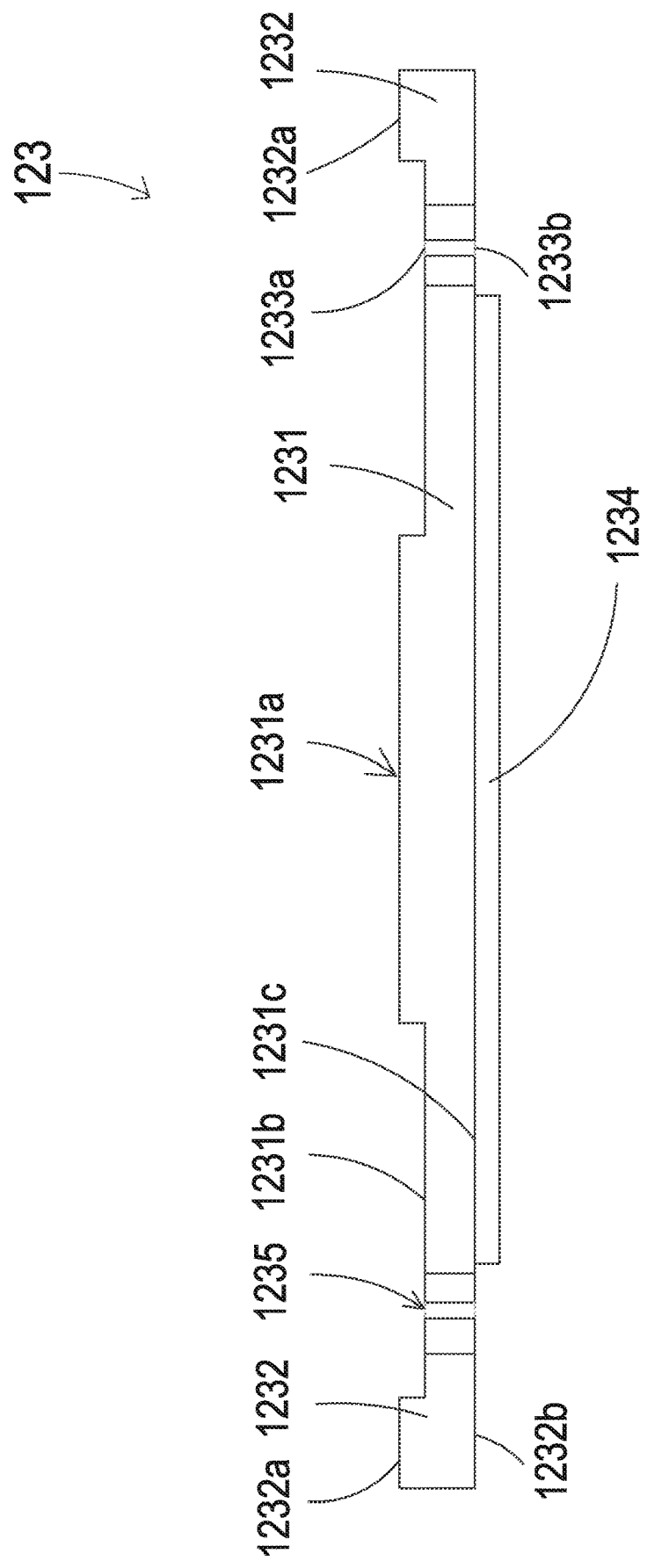
FIG. 4 illustrates a schematic cross-sectional view of a piezoelectric actuator according to an exemplary embodiment of the present disclosure.

Please further refer to FIG. 4. In this embodiment, the piezoelectric actuator 123 consists of a suspension plate 1231, an outer frame 1232, at least one supporting element 1233, and a piezoelectric sheet 1234. The piezoelectric sheet 1234 is attached to a second surface 1231c of the suspension plate 1231 so as to drive the suspension plate 1231 to bend and vibrate when the piezoelectric sheet 1234 is applied with a voltage. In this embodiment, the at least one supporting element 1233 is connected between the suspension plate 1231 and the outer frame 1232. Two ends of the at least one supporting element 1233 are respectively connected to the outer frame 1232 and the suspension plate 1231, thereby providing a flexible support for the suspension plate 1231. At least one gap 1235 is formed among the at least one supporting element 1233, the suspension plate 1231, and the outer frame 1232. The at least one gap 1235 is in communication with a gas pathway, so that the gas can be discharged out from the actuator 12A through the at least one gap 1235 and can be transmitted to the sensor 12B. Moreover, the outer frame 1232 is disposed around the periphery of the suspension plate 1231, and the outer frame 1232 has a conductive pin 1232c (as shown in FIG. 3B) extending outwardly for electrical connection, but is not limited thereto.

The suspension plate 1231 has a stepped structure. That is, the first surface 1231b of the suspension plate 1231 further has a protruding portion 1231a. The protruding portion 1231a may be a circular protruding structure, but is not limited thereto. The protruding portion 1231a of the suspension plate 1231 and the first surface 1232a of the outer frame 1232 are coplanar. The first surface 1231b of the suspension plate 1231 and the first surface 1233a of the supporting element 1233 are coplanar as well. Thus, there is a depth (a height difference) between the protruding portion 1231a of the suspension plate 1231 (the first surface 1232a of the outer frame 1232) and the first surface 1231b of the suspension plate 1231 (the first surface 1233a of the supporting element 1233). The second surface 1231c of the suspension plate 1231, the second surface 1232b of the outer frame 1232, and the second surface 1233b of the supporting element 1233 forms a flat coplanar structure. The piezoelectric sheet 1234 is attached to the second surface 1231c of the suspension plate 1231. In this embodiment, the side length of piezoelectric sheet 1234 is shorter than the side length of the suspension plate 1231.

In this embodiment, as shown in FIG. 3A, the first insulation sheet 124a, the conductive sheet 125, and the second insulation sheet 124b of the actuator 12A are sequentially disposed under the piezoelectric actuator 123. The shape of these elements also substantially corresponds to the shape of the outer frame 1232 of the piezoelectric actuator 123. In some embodiments, the first insulation sheet 124a and the second insulation sheet 124b are made of an insulation material (such as plastic, but not limited thereto) so as to provide insulation effect. In this embodiment, the conductive sheet 125 is made of a conductive material, for example but not limited to, a metal, so as to provide electrical conduction effect. In this embodiment, the conductive sheet 125 can also have a conductive pin 125a so as to achieve an electrical conduction effect.

Further, in this embodiment, as shown in FIG. 5, the inlet plate 121, the resonance sheet 122, the piezoelectric actuator 123, the first insulation sheet 124a, the conductive sheet 125, and the second insulation sheet 124b are sequentially stacked with each other to form the actuator 12A. Since a space h is between the resonance sheet 122 and the piezoelectric actuator 123, and a filling material for example but not limited to, a conductive adhesive is applied to the space h between the resonance sheet 122 and the periphery of the outer frame 1232 of the piezoelectric actuator 123. Therefore, a certain depth can be maintained between the resonance sheet 122 and the protruding portion 1231a of the suspension plate 1231 of the piezoelectric actuator 123, whereby the gas can be guided to flow more quickly. Moreover, since a proper distance is kept between the protruding portion 1231a of the suspension plate 1231 and the resonance sheet 122, the contact possibility between these components is decreased, and thus the noise can be reduced as well.

Please further refer to FIG. 3A, FIG. 3B, and FIG. 5. In this embodiment, after the inlet plate 121, the resonance sheet 122, and the piezoelectric actuator 123 are sequentially stacked and assembled with each other, the resonance sheet 122 has a movable portion 122a and a fixed portion 122b. The movable portion 122a and the inlet plate 121 above the movable portion 122a together form a chamber for converging the gas. A first chamber 120 is further formed between the resonance sheet 122 and the piezoelectric actuator 123 for temporarily storing the gas. The first chamber 120 is in communication with the chamber formed by the central recess 121c of the inlet plate 121 through the perforation 122c of the resonance sheet 122. The two sides of the first chamber 120 are in communication with the gaps 1235 between the supporting elements 1233 of the piezoelectric actuator 123, so that the first chamber 120 is in communication with the gas pathway.

Figure 6A:
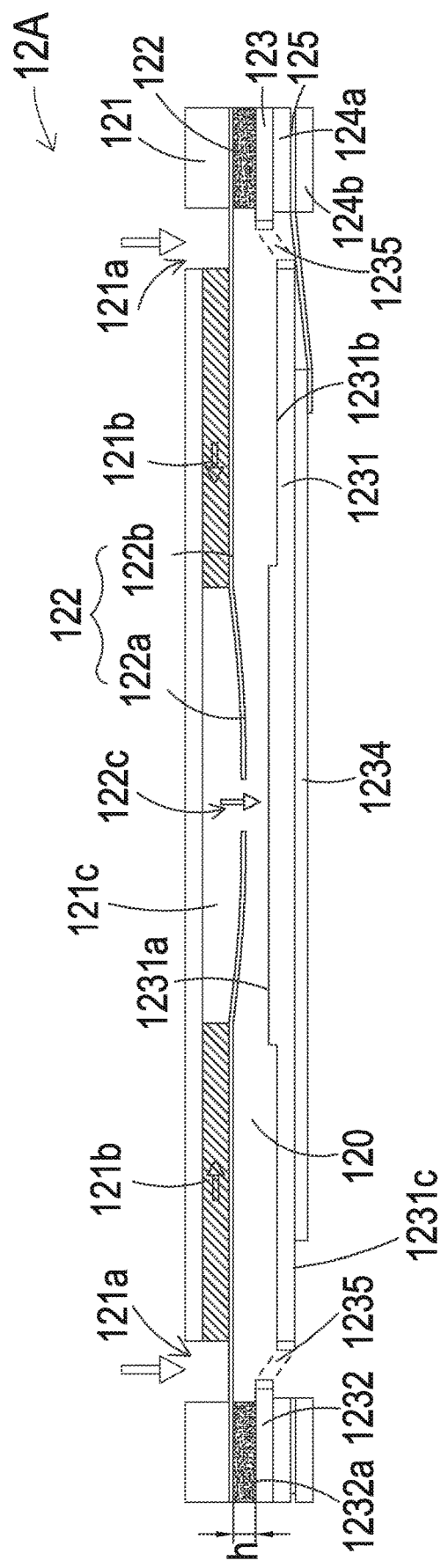
FIG. 6A and FIG. 6B illustrate schematic cross-sectional views showing the piezoelectric pump according to the first embodiment of the present disclosure at different operation steps.
Figure 6B:
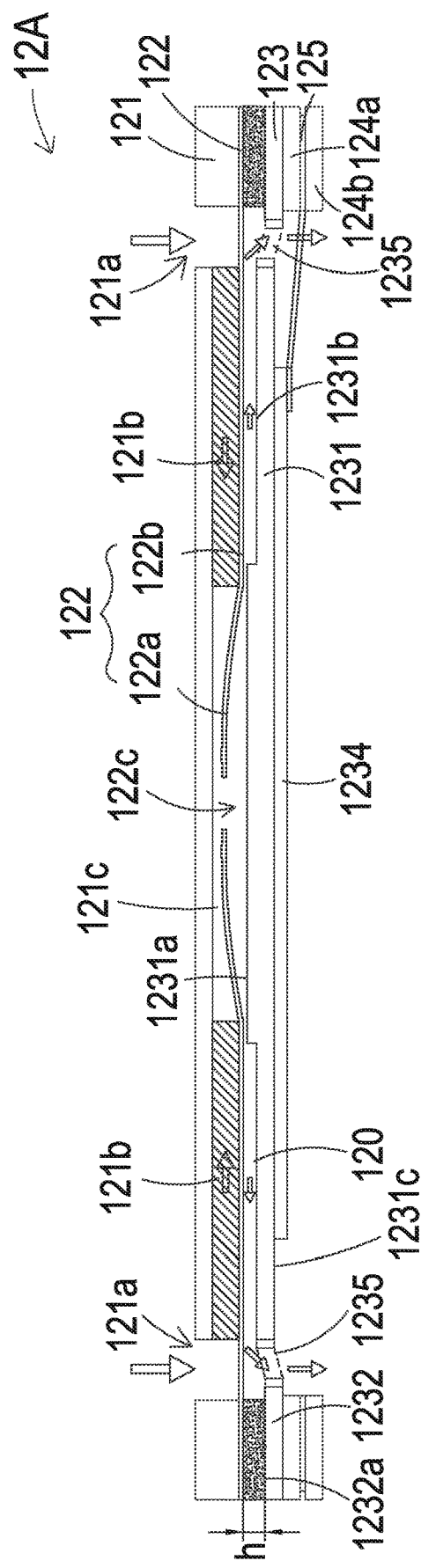

Please refer to FIG. 3A, FIG. 3B, FIG. 5, FIG. 6A, and FIG. 6B. The operation of the actuator 12A according to one embodiment of the present disclosure is described as below. When the actuator 12A begins to operate, the piezoelectric actuator 123 is driven by a voltage and then starts to bend and vibrate vertically and reciprocatingly by taking the supporting elements 1233 as pivots. As shown in FIG. 6A, when the piezoelectric actuator 123 is driven by a voltage and bends downwardly, since the resonance sheet 122 is a light and thin sheet, the resonance sheet 122 will perform a vertical reciprocating vibration corresponding to the piezoelectric actuator 123. That is, the portion of the resonance sheet 122 corresponding to the central recess 121c will bend and vibrate along with the piezoelectric actuator 123. Thus, the portion of the resonance sheet 122 corresponding to the central recess 121c is the movable portion 122a of the resonance sheet 122. When the piezoelectric actuator 123 bends downwardly, because of the introduction and pushing of the gas to the movable portion 122a and the driving of the piezoelectric actuator 123 by the vibration of the piezoelectric actuator 123, the movable portion 122a corresponding to the central recess 121c of the resonance sheet 122 also bends downwardly along with the piezoelectric actuator 123. Hence, the gas outside the actuator 12A flows into the inlet plate 121 through the at least one inlet hole 121a of the inlet plate 121, and the gas is converged at the central recess 121c through the at least one convergence channel 121b. Then, the gas flows downwardly into the first chamber 120 through the perforation 122c of the resonance sheet 122 corresponding to the central recess 121c. Thereafter, since the resonance plate 122 is driven by the vibration of the piezoelectric actuator 123, the resonance plate 122 will also resonate with the piezoelectric actuator 123 and perform vertical reciprocating vibration. As shown in FIG. 6B, when the piezoelectric actuator 123 is driven to bend upwardly, the movable portion 122a of the resonance sheet 122 bends upwardly correspondingly. Therefore, the volume of the first chamber 120 can be compressed by the piezoelectric actuator 123, and the middle gas path of the first chamber 120 is closed. Accordingly, the gas in the first chamber 120 is pushed to flow toward the two sides of the first chamber 120, and the gas further passes through the gaps 1235 between the supporting elements 1233 of the piezoelectric actuator 123 and then flow downwardly. By repeating the actions of the actuator 12A as shown in FIG. 6A and FIG. 6B, since the gas pathway design of the actuator 12A can generate a gas pressure gradient in the actuator 12A, the gas can be pushed to flow in a high speed. Moreover, through the resistance difference of the gas path way in different flow directions, the gas will be transmitted from the suction end to the discharge end, thereby achieving a gas transmission. Moreover, even in the case that the discharge end is under a pressure, the actuator 12A can still continue to push the gas into the gas pathway, and the noise of the actuator 12A can be reduced as well.

Figure 2:
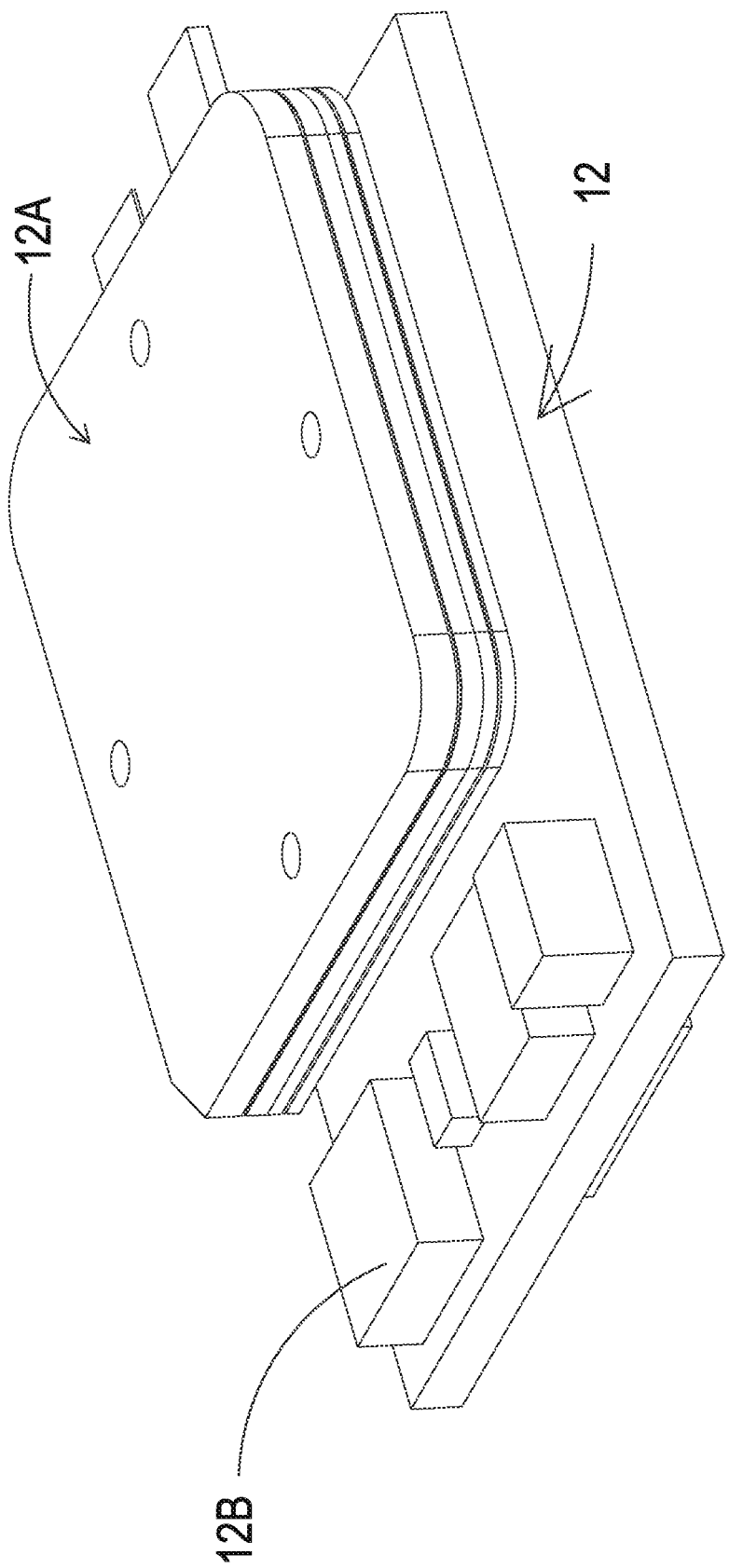
FIG. 2 illustrates a perspective view of components of an actuator-sensor module according to an exemplary embodiment of the present disclosure.
Figure 7A:
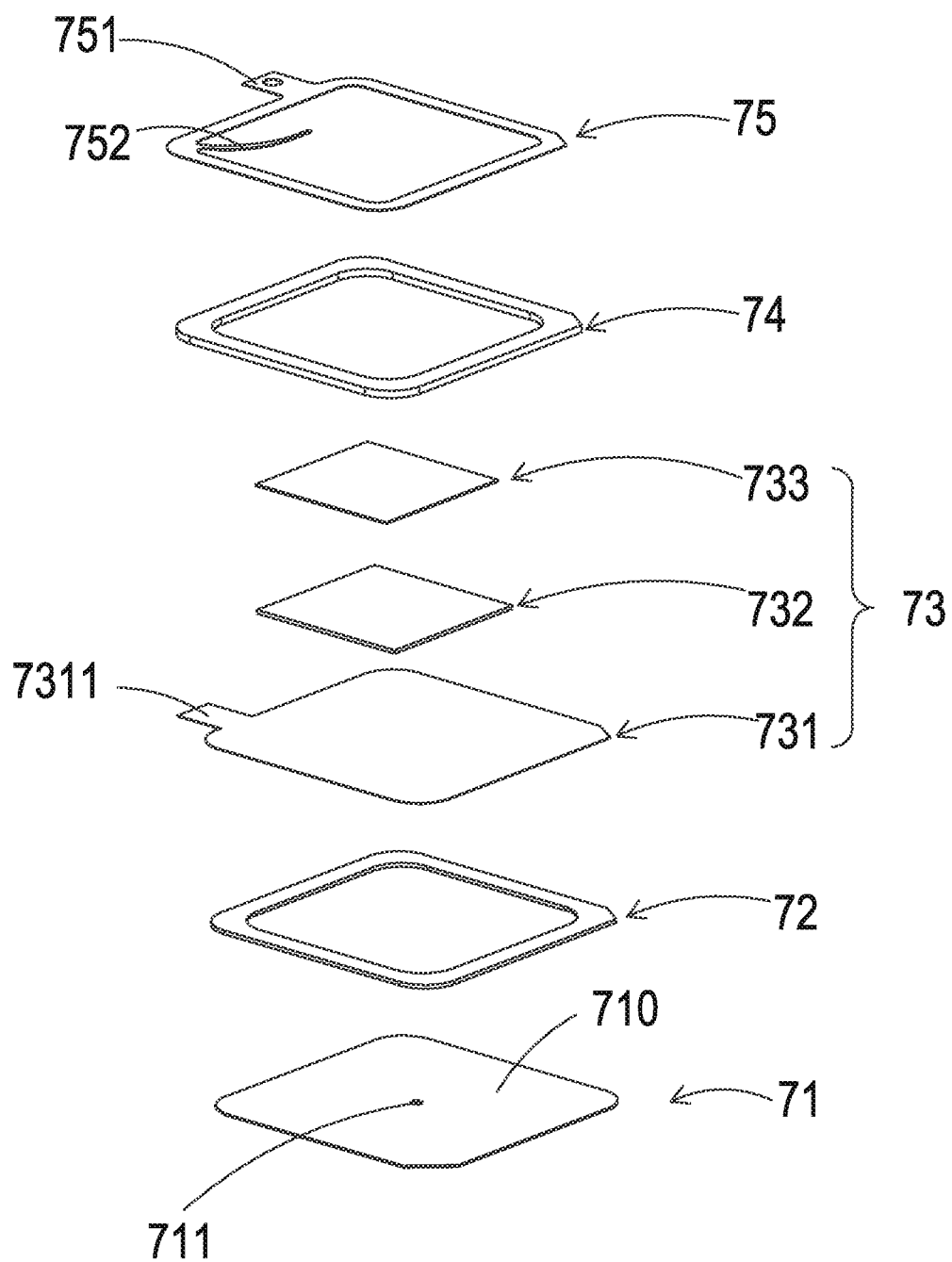
FIG. 7A and FIG. 7B respectively illustrate a front exploded view and a rear exploded view of a piezoelectric pump according to the second embodiment of the present disclosure.
Figure 7B:
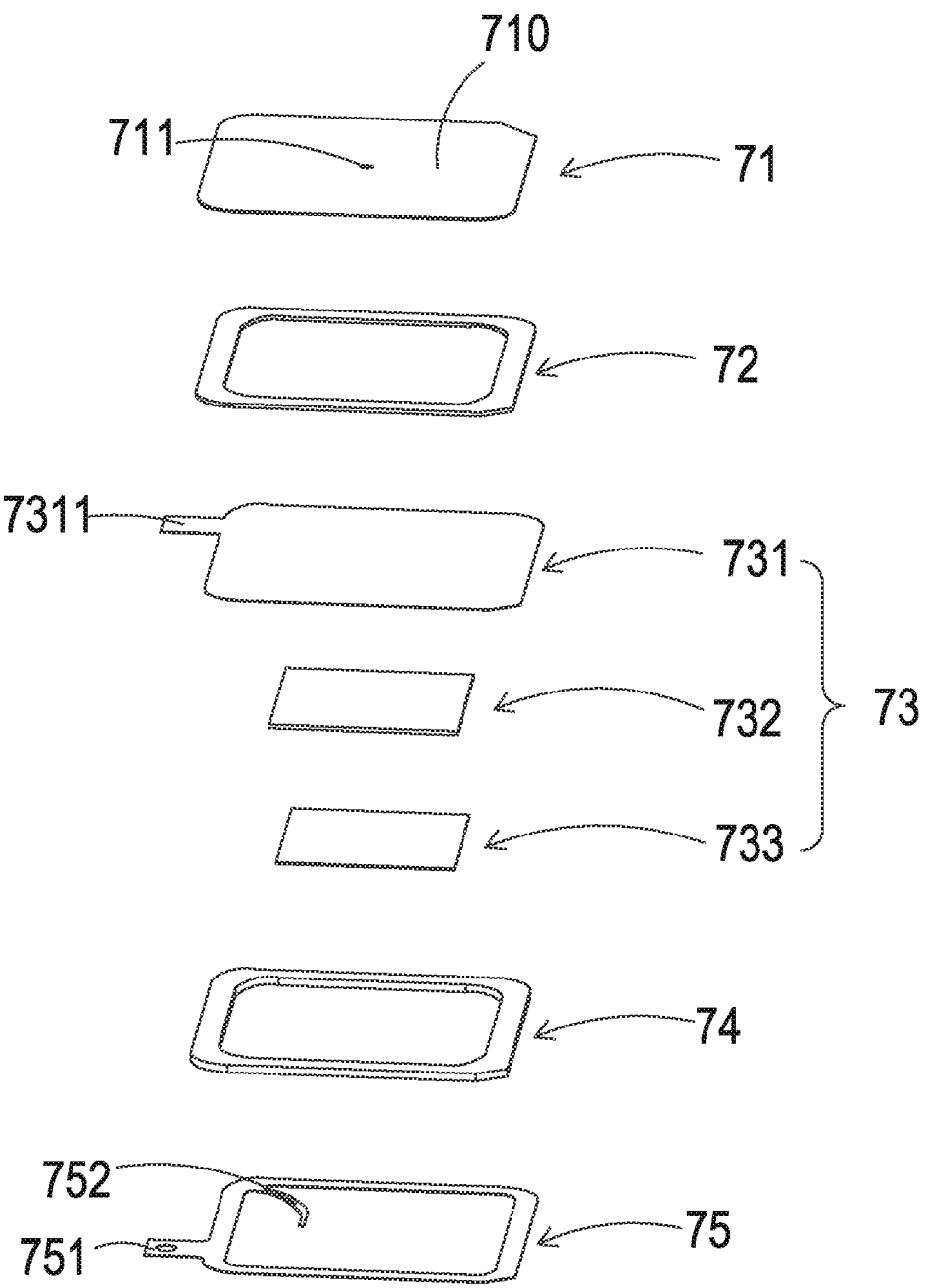

Please refer to FIG. 7A and FIG. 7B, which show the structure of the piezoelectric pump according to the second embodiment of the present disclosure. The actuator 12A (as shown in FIG. 1 and FIG. 2) includes a nozzle plate 71, a chamber frame 72, an actuating body 73, an insulation frame 74, and a conductive frame 75.

The nozzle plate 71 is made of a flexible material, and the nozzle plate 71 has a suspension sheet 710 and a hollow hole 711. The suspension sheet 710 is a flexible sheet which can bend and vibrate. The shape of the suspension sheet 710 may be square, circle, ellipse, triangle or polygon. The hollow hole 711 is defined through the center portion of the suspension sheet 710 for allowing the gas flowing therethrough.

The chamber frame 72 is stacked on the nozzle plate 71, and the shape of the chamber frame 72 corresponds to the shape of the nozzle plate 71. The actuating body 73 is stacked on the chamber frame 72. A resonance chamber 76 is between the chamber frame 72 and the suspension sheet 710. The insulation frame 74 is stacked on the actuating body 73. The appearance of the insulation frame 74 is similar to that of the chamber frame 72. The conductive frame 75 is stacked on the insulation frame 74. The appearance of the conductive frame 75 is similar to that of the insulation frame 74. The conductive frame 75 has a conductive frame pin 751 and a conductive electrode 752. The conductive frame pin 751 extends outwardly from the outer edge of the conductive frame 75, and the conductive electrode 752 extends inwardly from the inner edge of the conductive frame 75. Moreover, the actuating body 73 further includes a piezoelectric carrier plate 731, an adjusting resonance plate 732, and a piezoelectric plate 733. The piezoelectric carrier plate 731 is stacked on the chamber frame 72. The adjusting resonance plate 732 is stacked on the piezoelectric carrier plate 731. The piezoelectric plate 733 is stacked on the adjusting resonance plate 732. The adjusting resonance plate 732 and the piezoelectric plate 733 are accommodated in the insulation frame 74. The conductive electrode 752 of the conductive frame 75 is electrically connected to the piezoelectric plate 733. The piezoelectric carrier plate 731 and the adjusting resonance plate 732 are both made of the same conductive material or different conductive materials. The piezoelectric carrier plate 731 has a piezoelectric pin 7311. The piezoelectric pin 7311 and the conductive frame pin 751 are used for electrical connection so as to receive a driving signal (a driving frequency and a driving voltage), but is not limited thereto. The piezoelectric pin 7311, the piezoelectric carrier plate 731, the adjusting resonance plate 732, the piezoelectric plate 733, the conductive electrode 752, the conductive frame 75, and the conductive frame pin 751 may together form a part of a circuit, and the insulation frame 74 is provided for electrically isolating the conductive frame 75 and the actuating body 73 for avoiding short circuit, whereby the driving signal can be transmitted to the piezoelectric plate 733. When the piezoelectric plate 733 receives the driving signal (a driving frequency and a driving voltage), the piezoelectric plate 733 deforms owing to the piezoelectric effect, and thus the piezoelectric carrier plate 731 and the adjusting resonance plate 732 are driven to perform vertical and reciprocating vibration correspondingly.

As mentioned above, the adjusting resonance plate 732 is disposed between the piezoelectric plate 733 and the piezoelectric carrier plate 731. As a result, the adjusting resonance plate 732 can serve as a buffer element between the piezoelectric plate 733 and the piezoelectric carrier plate 731, whereby the vibration frequency of the piezoelectric carrier plate 731 can be adjusted. Generally, the thickness of the adjusting resonance plate 732 is greater than the thickness of the piezoelectric carrier plate 731. The thickness of the adjusting resonance plate 732 may be changed so as to adjust the vibration frequency of the actuating body 73.

Please refer to FIG. 7A, FIG. 7B, and FIG. 8A. The nozzle plate 71, the chamber frame 72, the actuating body 73, the insulation frame 74, and the conductive frame 75 are sequentially stacked and assembled with each other on one surface of the actuator-sensor module 12, so that the piezoelectric pump is placed and positioned on the actuator-sensor module 12. The piezoelectric pump is supported by the positioning bumps 12C, so that a spacing distance 712 is between the suspension sheet 710 of the piezoelectric pump and the surface of the actuator-sensor module 12 for the gas to pass therethrough.

Please further refer to FIG. 8A, a gas flow chamber 77 is formed between the nozzle plate 71 and the surface of the actuator-sensor module 12. The gas flow chamber 77 is in communication with, through the hollow hole 711 of the nozzle plate 71, the resonance chamber 76 formed among the actuating body 73, the chamber frame 72, and the suspension sheet 710. By controlling the vibration frequency of the gas in the resonance chamber 76 to be the same as the vibration frequency of the suspension sheet 710, the resonance chamber 76 and suspension sheet 710 can generate the Helmholtz resonance effect so as to improve the transmission efficiency of the gas.

Figure 8B:
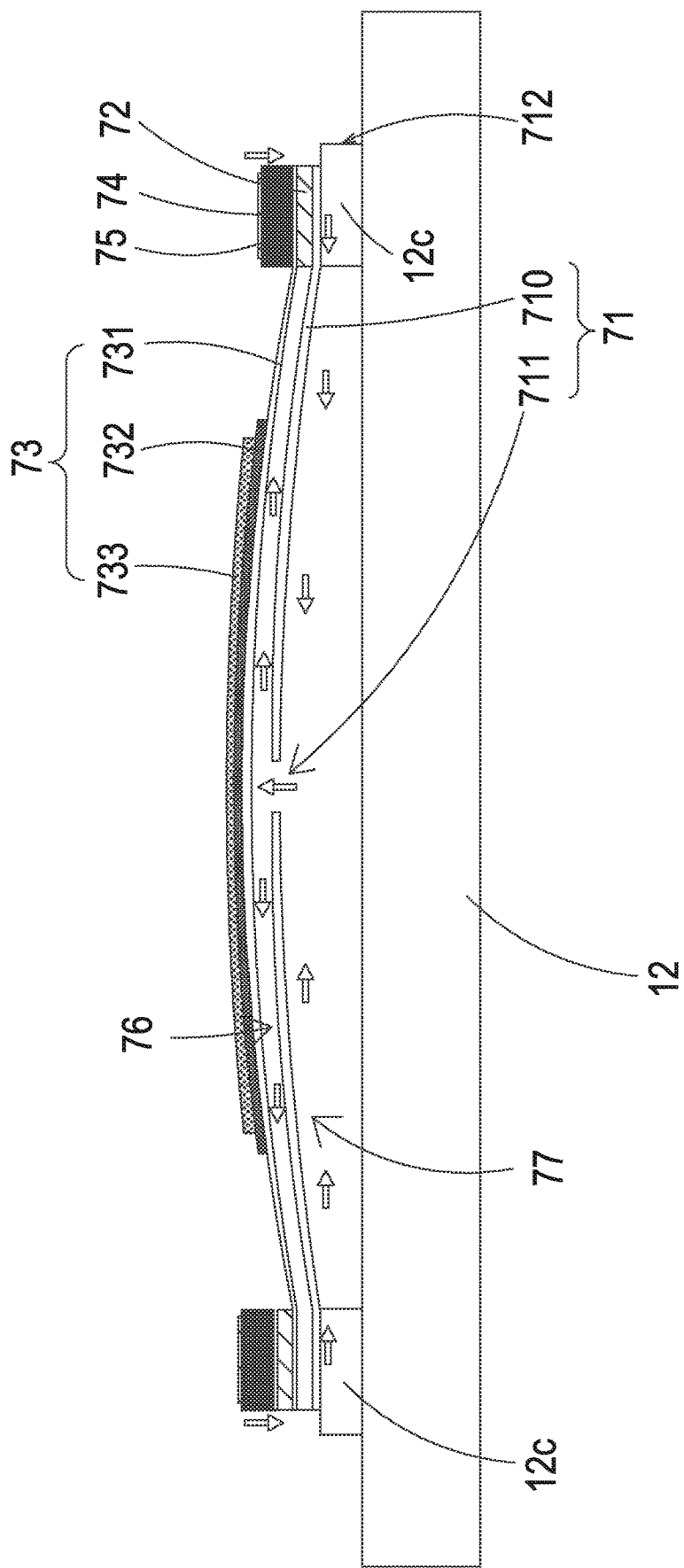
FIG. 8B to FIG. 8C illustrate schematic cross-sectional views showing the piezoelectric pump according to the second embodiment of the present disclosure at different operation steps.
Figure 8C:
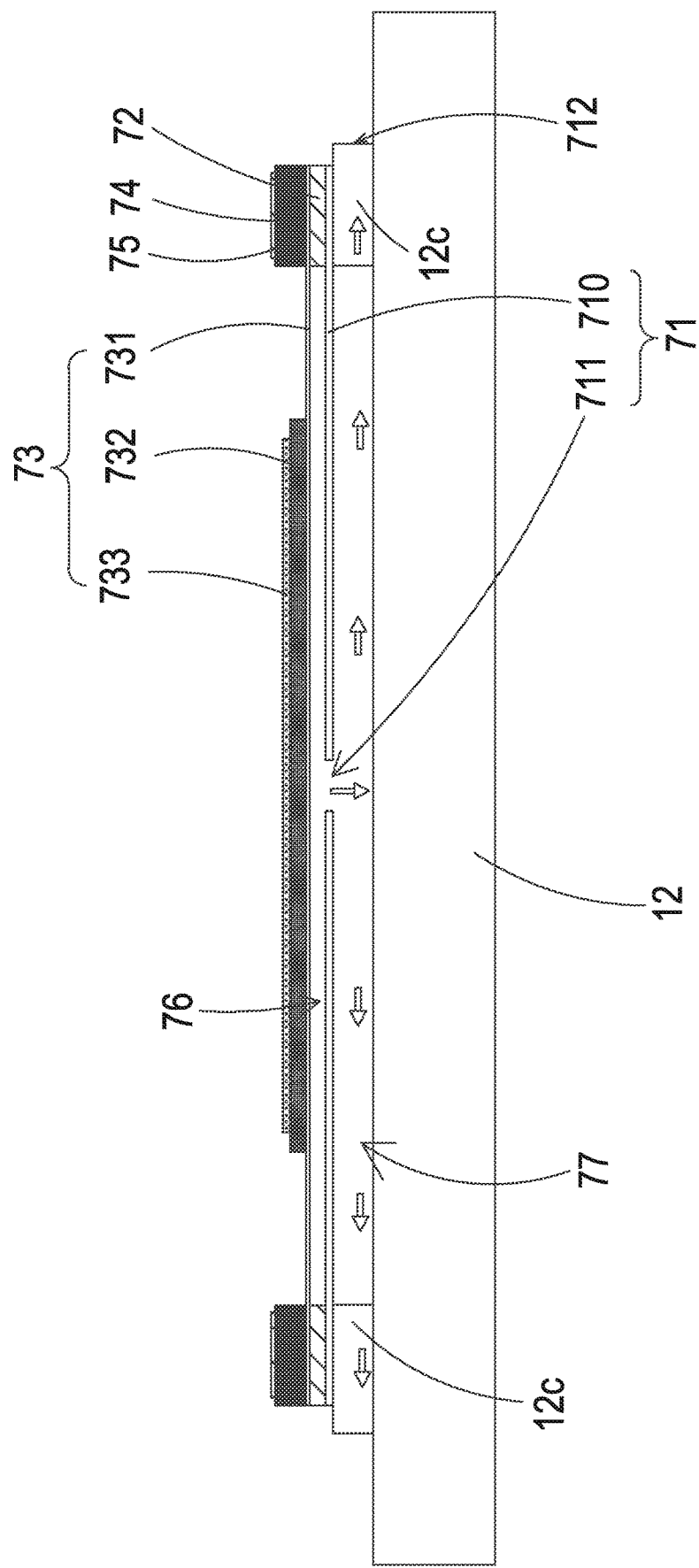

FIG. 8B and FIG. 8C illustrate schematic cross-sectional views showing the piezoelectric pump of FIG. 8A at different operation steps. Please refer to FIG. 8B first. When the piezoelectric plate 733 bends toward a direction away from the surface of the actuator-sensor module 12, the suspension sheet 710 of the nozzle plate 71 is driven to bend toward the direction away from the surface of the actuator-sensor module 12 correspondingly. Hence, the volume of the gas flow chamber 77 expands quickly, so that the inner pressure of the gas flow chamber 77 decreases and becomes negative, thereby drawing the gas outside the piezoelectric pump to flow into the piezoelectric pump through the spacing distance 712. The gas further enters into the resonance chamber 76 through the hollow hole 711, thereby increasing the gas pressure of the resonance chamber 76 and thus generating a pressure gradient. As shown in FIG. 8C, when the piezoelectric plate 733 drives the suspension sheet 710 of the nozzle plate 71 to move toward the surface of the actuator-sensor module 12, the gas inside the resonance chamber 76 is pushed to flow out quickly through the hollow hole 711 so as to further push the gas inside the gas flow chamber 77, whereby the converged gas can be quickly and massively ejected and guided into the sensor 12B of the actuator-sensor module 12 in a state closing to an ideal gas state under the Benulli's law. Therefore, by repeating the steps as shown in FIG. 8B and FIG. 8C, the piezoelectric plate 733 can bend and vibrate vertically and reciprocatingly. Further, after the gas is discharged out of the resonance chamber 76, the inner pressure of the resonance chamber 76 is lower than the equilibrium pressure due to the inertia, thereby the pressure difference guiding the gas outside the resonance chamber 76 into the resonance chamber 76 again. Thus, by controlling the vibration frequency of the gas inside the resonance chamber 76 to be the same as the vibration frequency of the piezoelectric plate 733 in such way to generate the Helmholtz resonance effect, high-speed and large-volume gas transmission can be achieved.

Figure 9A:
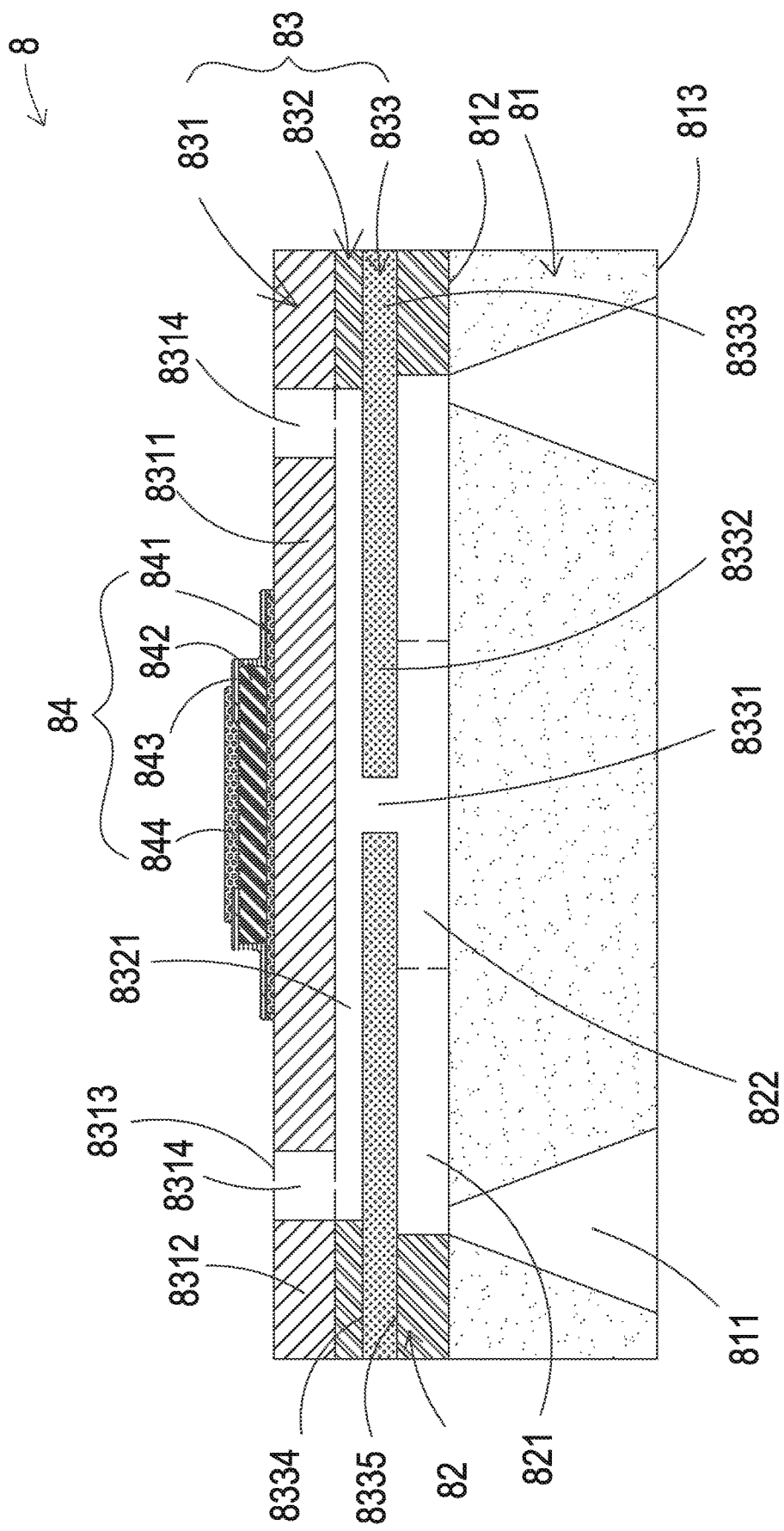
FIG. 9A illustrates a schematic cross-sectional view of a micro-electromechanical systems pump according to an exemplary embodiment of the present disclosure.
Figure 9B:
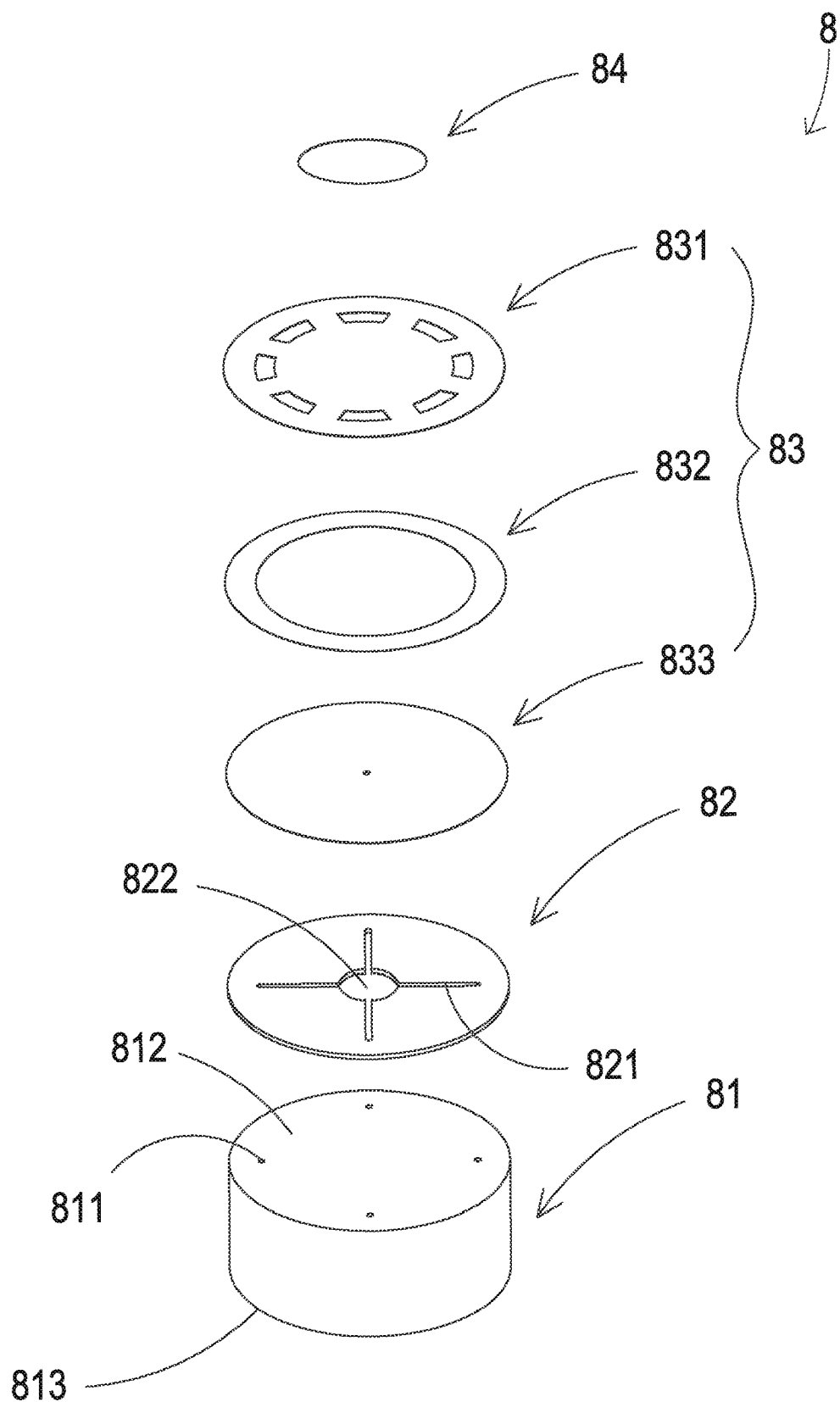
FIG. 9B illustrates a front exploded view of the micro-electromechanical systems pump of the present disclosure.

Please refer to FIG. 9A and FIG. 9B, which show another embodiment of the actuator 12A (as shown in FIG. 1 and FIG. 2) of the present disclosure. The following paragraphs describe the structure of the micro-electromechanical systems pump 8. The micro-electromechanical systems pump 8 includes a first substrate 81, a first oxide layer 82, a second substrate 83, and a piezoelectric element 84.

The first substrate 81 is a silicon wafer (Si wafer), and the thickness of the Si wafer may be between 150 and 400 μm (micrometer). The first substrate 82 has a plurality of inlets 811, a substrate first surface 812, and a substrate second surface 813. In this embodiment, the number of the inlets 811 is four, but not limited thereto. Each of the inlets 811 is defined through the first substrate 81 from the substrate second surface 813 to the substrate first surface 812. In order to improve the inflow efficiency of the inlets 811, each of the inlets 811 is a conical hole, that is, each of the inlets 811 is conical and tapered from the substrate second surface 813 to the substrate first surface 812.

The first oxide layer 82 is a silicon dioxide ($SiO_2$) film. The thickness of the $SiO_2$ film is between 10 and 20 μm. The first oxide layer 82 is stacked on the substrate first surface 812 of the first substrate 82. The first oxide layer 82 has a plurality of convergence troughs 821 and an oxide layer convergence chamber 822. The number and the position of the convergence troughs 821 correspond to the number and the position of the inlets 811 in the first substrate 81. In this embodiment, the number of the convergence troughs 821 is four as well. One end of each of the four convergence troughs 821 is in communication with the corresponding inlet 811 in the first substrate 82. The other end of each of the four convergence troughs 821 is in communication with the oxide layer convergence chamber 822. Thus, after a fluid enters into the first substrate 82 from the inlets 811, the fluid converges at the oxide layer convergence chamber 822 after flowing through the corresponding convergence troughs 821.

The second substrate 83 is a silicon-on-insulator (SOI) wafer, which includes a silicon wafer layer 831, a second oxide layer 832, and a silicon material layer 833. The thickness of the silicon wafer layer 831 is between 10 and 20 μm. In some embodiments, the silicon wafer layer 831 has an actuation portion 8311, an outer peripheral portion 8312, a plurality of connection portions 8313, and a plurality of fluid channels 8314. The actuation portion 8311 is circular. The outer peripheral portion 8312 is in a hollow ring shape and surrounds the periphery of the actuation portion 8311. The connection portions 8313 are respectively located between and connected between the actuation portion 8311 and the outer peripheral portion 8312 for providing an elastic support for the actuation portion 8311. The fluid channels 8314 surround the periphery of the actuation portion 8311 and are located between the plurality of connection portions 8313.

The thickness of the second oxide layer 832 is between 0.5 and 2 μm. The second oxide layer 832 is formed on the silicon wafer layer 831. The second oxide layer 832 is in a hollow ring shape, and the second oxide layer 832 and the silicon wafer layer 831 together define a vibration chamber 8321. The silicon material layer 833 is in a circular shape and stacked on the second oxide layer 832. The silicon material layer 833 is combined with the first oxide layer 82. The silicon material layer 833 is a silicon dioxide ($SiO_2$) film, and the thickness of the silicon material layer 833 may be between 2 and 5 μm. The silicon material layer 833 has a through hole 8331, a vibration portion 8332, a fixed portion 8333, a third surface 8334, and a fourth surface 8335. The through hole 8331 may be located at a center portion of the silicon material layer 833. The vibration portion 8332 may be located at a peripheral area of the through hole 8331, and the vibration portion 8332 may be perpendicularly corresponding to the vibration chamber 8321. The fixed portion 8333 may be located at a peripheral area of the silicon material layer 833, and the vibration portion 8332 is fixed to the second oxide layer 832 by the fixed portion 8333. The third surface 8334 is assembled with the second oxide layer 832, and the fourth surface 8335 is assembled with the first oxide layer 82. The piezoelectric element 84 is stacked on the actuation portion 8311 of the silicon wafer layer 831.

The piezoelectric element 84 includes a lower electrode layer 841, a piezoelectric layer 842, an insulation layer 843, and an upper electrode layer 844. The lower electrode layer 841 may be stacked on the actuation portion 8311 of the silicon wafer layer 831, and the piezoelectric layer 842 may be stacked on the lower electrode layer 841. The piezoelectric layer 842 and the lower electrode layer 841 are electrically connected through the contacted area between each other. Moreover, the width of the piezoelectric layer 842 may be smaller than the width of the lower electrode layer 841, and thus the lower electrode layer 841 is not completely covered by the piezoelectric layer 842. The insulation layer 843 may be stacked on part of the piezoelectric layer 842 and the remaining portion of the surface of the lower electrode layer 841 which is not covered by the piezoelectric layer 842. Then, the upper electrode layer 844 may be stacked on the insulation layer 843 and the remaining portion of the surface of the piezoelectric layer 842 which is not covered by the insulation layer 843, and thus the upper electrode layer 844 may be electrically connected to the piezoelectric layer 842 through the contact between each other. Moreover, since the insulation layer 843 is inserted between the upper electrode layer 844 and the lower electrode layer 841, a short circuit condition caused by the direct contact between the upper electrode layer 844 and the lower electrode layer 841 could be avoided.

Figure 10A:
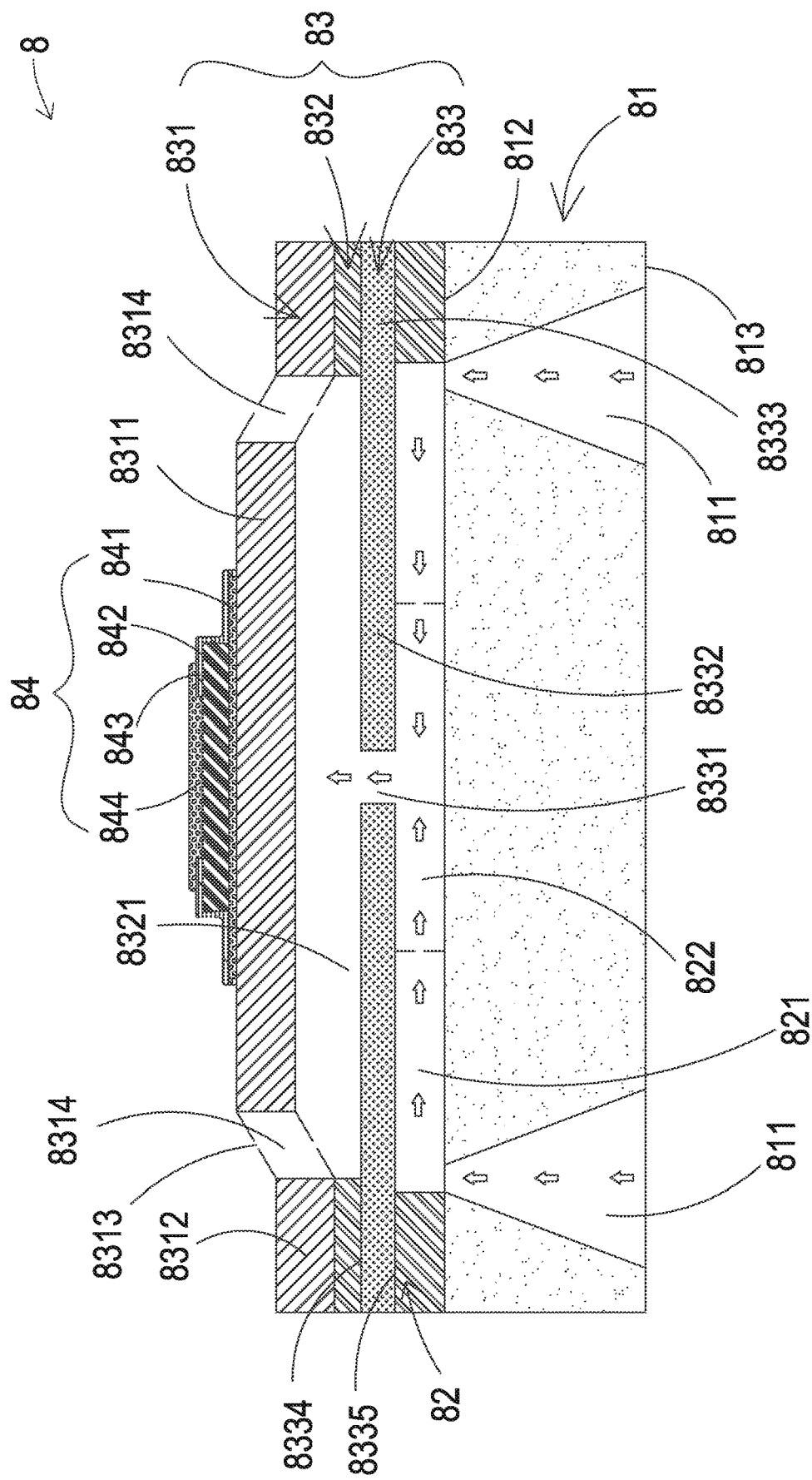
FIG. 10A to FIG. 10C illustrate schematic cross-sectional views showing the micro-electromechanical systems pump of the present disclosure at different operation steps.
Figure 10B:
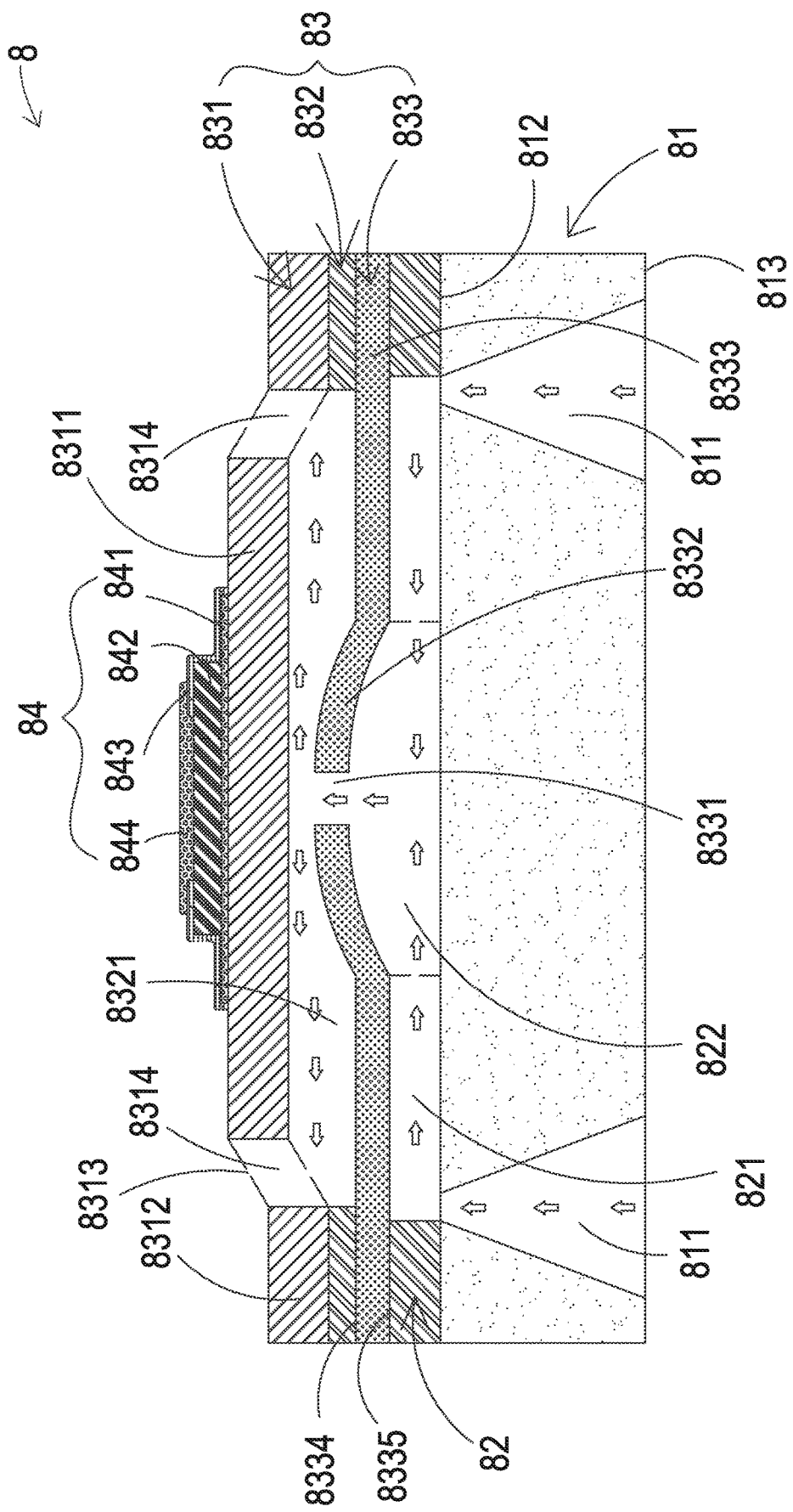
Figure 10C:
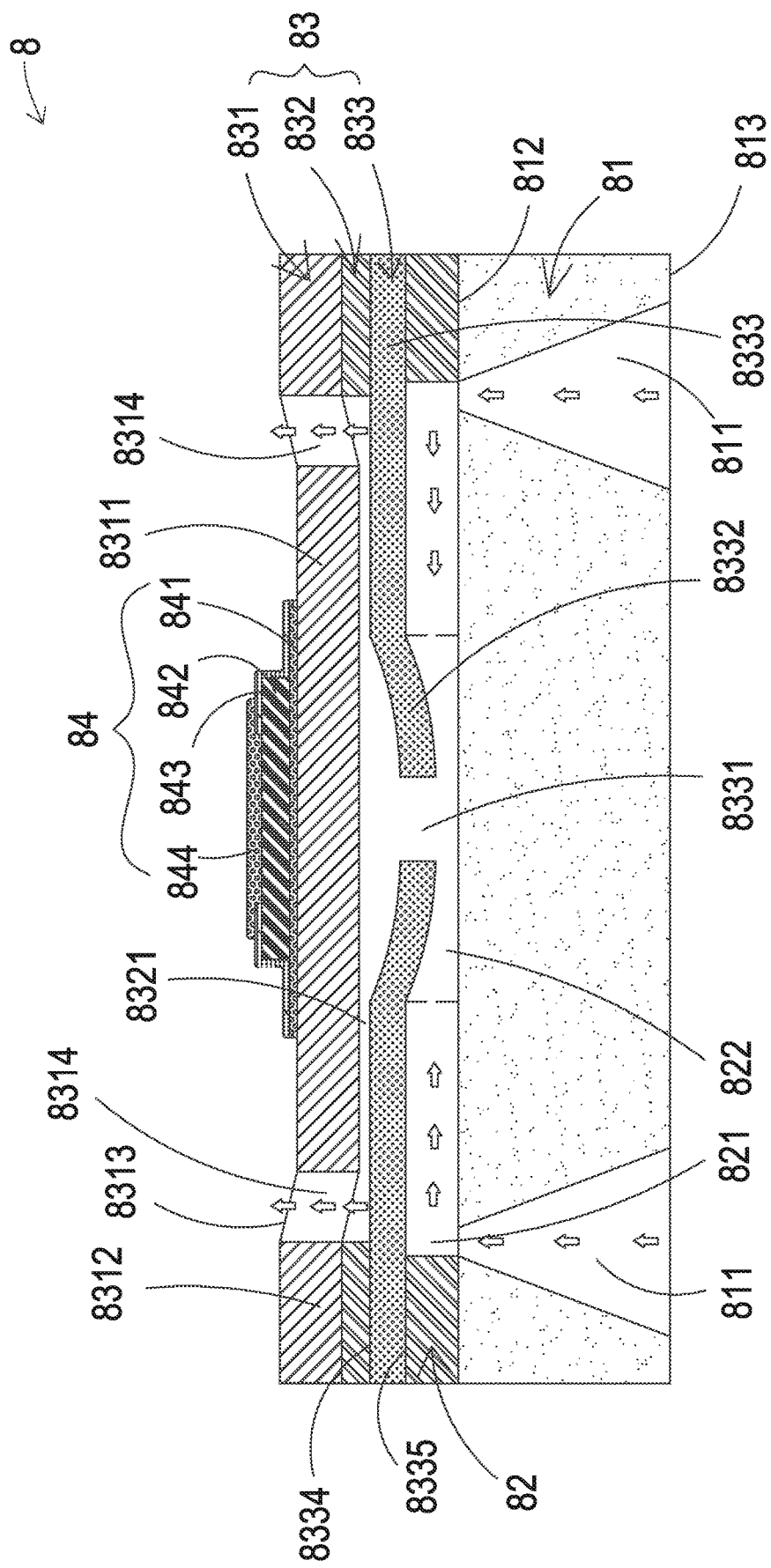

FIG. 10A to FIG. 10C illustrate schematic cross-sectional views showing the micro-electromechanical systems pump 8 of the present disclosure at different operation steps. Please refer to FIG. 10A first, when the lower electrode layer 841 and the upper electrode layer 844 of the piezoelectric element 84 receive a driving voltage and a driving signal (not shown in the figure), the voltage and the signal are transmitted to the piezoelectric layer 842. After the piezoelectric layer 842 is applied with the driving voltage and the driving signal, the piezoelectric layer 842 starts to deform because of the reverse piezoelectric effect, thereby driving the actuation portion 8311 of the silicon wafer layer 831 to move correspondingly. When the actuation portion 8311 is driven upwardly by the piezoelectric element 84 and thus the distance between the actuation portion 8311 and the second oxide layer 832 increases, the volume of the vibration chamber 8321 in the second oxide layer 832 increases as well. Hence, the pressure in the vibration chamber 8321 becomes negative, and thus the gas in the oxide layer convergence chamber 822 of the first oxide layer 82 is drawn into the vibration chamber 8321 through the through hole 8331. Please refer to FIG. 10B, when the actuation portion 8311 is driven upwardly by the piezoelectric element 84, the vibration portion 8332 of the silicon material layer 833 is moved upwardly due to the resonance effect. When the vibration portion 8332 is moved upwardly, the space of the vibration chamber 8321 is compressed and the fluid in the vibration chamber 8321 is pushed to fluid channels 8314 of the silicon wafer layer 831, so that the fluid can be discharged upwardly through the fluid channels 8314. When the vibration portion 8332 is moved upwardly to compress the space of the vibration chamber 8321, the volume of the oxide layer convergence chamber 822 increases owing to the movement of the vibration portion 8332. Hence, the pressure in the oxide layer convergence chamber 822 becomes negative, and thus the fluid outside of the MEMS pump 8 is drawn into the oxide layer convergence chamber 822 through the inlets 811. In the last step, as shown in FIG. 10C, when the actuation portion 8311 of the silicon wafer layer 831 is driven downwardly by the piezoelectric element 84, the fluid in the vibration chamber 8321 is pushed to the fluid channels 8314 and then discharged out. The vibration portion 8332 of the silicon material layer 833 is also driven by the actuation portion 8311 and thus moved downwardly; at the same time, the vibration portion 8332 compresses the fluid in oxide layer convergence chamber 822 and forces the fluid to move to the vibration chamber 8321 through the through hole 8331. Accordingly, when the actuation portion 8311 is driven upwardly by the piezoelectric element 84 again later, the volume of the vibration chamber 8321 greatly increases, thereby generating a larger suction force to draw the gas into the vibration chamber 8321. By repeating the aforementioned steps, the actuation portion 8311 can be continually driven by the piezoelectric element 84 to move upwardly and downwardly, and the vibration portion 8332 is also driven to move upwardly and downwardly correspondingly. Thus, the internal pressure of the MEMS pump 8 can be changed periodically so as to draw and discharge the fluid continually, thereby completing the pumping process of the MEMS pump 8.

Accordingly, by disposing the sensor 12B at one side of the actuator 12A in the actuator-sensor module 12, since the actuator 12A can be driven to move so as to guide the gas to pass through the sensor 12B, the sensor 12B can be provided with a stable and consistent gas flow, so that the sensor 12B can measure and/or detect the received gas directly, and the detection time of the sensor 12B can be reduced as well, thereby achieving an accurate and real-time monitoring.

Please refer back to FIG. 1. The monitoring module 11 captures an image of the corresponding fixed position, stores the image, converts the image into an image data, and outputs the image data. The actuator-sensor module 12 is installed in the monitoring module 11. The actuator-sensor module 12 includes at least one actuator 12A and at least one sensor 12B. The actuator 12A guides the gas outside the monitoring module 11 into the monitoring module 11. The sensor 12B detects the gas so as to generate a gas detecting data and output the gas detecting data. The microprocessor 13 converts the image captured by the monitoring module 11 into the image data and outputs the image data. The microprocessor 13 also converts a gas detecting value generated by the actuator-sensor module 12 into the gas detecting data, and outputs the gas detecting data. The microprocessor further transmits the image data and the gas detecting data to the data transmitter 14, and the image data and the gas detecting data is transmitted to the cloud data processing device 2 through the data transmitter for being stored and intelligently analyzed. The cloud data processing device 2 may combine the analyzed outcomes with a map data as well as a meteorological data to generate a processed data (e.g. a real-time air quality map) and to form a monitoring database. The processed data can be transmitted to a notification processing system 3, so that the notification processing system 3 may start a monitoring notification processing mechanism device 3A, and the monitoring notification processing mechanism device 3A transmits the monitoring notification information to a user device, or the notification processing system 3 may start an air quality notification processing mechanism device 3B, and the air quality notification processing mechanism device 3B transmits the air quality notification information to a user device. From the above descriptions, it can be understood that, one object of the present disclosure is providing a monitoring and gas detection information notification system which combines an actuator-sensor module 12 with a micro monitoring device 1 for a further application. By using a plurality of monitoring devices 1 respectively disposed at different places, the air information of the places where the monitoring devices 1 respectively locate can be monitored in real time. Therefore, a real-time monitoring of the air quality around the human can be achieved and can be easily popularized. Furthermore, by further establishing a data connection between the cloud data processing device 2 and the monitoring devices 1 through a data network, the user device can inquire and obtain needed notification information through the monitoring and gas detection information notification system.

To sum up, the present disclosure provides a monitoring and gas detection information notification system which combines an actuator-sensor module 12 with a micro monitoring device 1 for a further application. By using a plurality of monitoring devices 1 respectively disposed at different places, the air information of the places where the monitoring devices 1 locate can be monitored in real time. Therefore, a real-time monitoring of the air quality around the human can be achieved and can be easily popularized. Furthermore, by further establishing a data connection between the cloud data processing device 2 and the monitoring devices through a data network, the system not only can provide a notification processing mechanism required for monitoring, but also can provide more accurate and real-time air quality monitoring information and maps for starting an air quality notification processing mechanism. The industrial value of the present application is very high, so the application is submitted in accordance with the law.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A monitoring and gas detection information notification system, comprising:
 a plurality of monitoring devices, wherein the plurality of monitoring devices are respectively disposed at corresponding fixed positions, and each of the plurality of monitoring devices comprises:
  a monitoring module capturing an image of the corresponding fixed position, storing the image, converting the image into an image data, and outputting the image data; and
  an actuator-sensor module installed in the monitoring module, wherein the actuator-sensor module comprises at least one actuator and at least one sensor, wherein the at least one actuator guides a gas outside the monitoring module into the monitoring module, and the at least one sensor detects the gas so as to generate a gas detecting data and output the gas detecting data; and
 a cloud data processing device storing and intelligently analyzing the image data output by the monitoring module and the gas detecting data output by the actuator-sensor module, wherein the image data and the gas detecting data are transmitted to the cloud data processing device by the monitoring module through a data network to generate a processed data, and the cloud data processing device transmits the processed data to a notification processing system so as to conduct a notification of monitoring information and gas detecting information;
 wherein the notification processing system starts a monitoring notification processing mechanism device, wherein the monitoring notification processing mechanism device is adapted to transmit a monitoring notification information to a user device.

2. The monitoring and gas detection information notification system according to claim 1, wherein each of the plurality of the monitoring devices further comprises a microprocessor and a data transmitter, wherein the microprocessor controls an operation of the monitoring module and an operation of the actuator-sensor module, converts the image captured by the monitoring module into the image data and outputs thereof, and converts a gas detecting value generated by the actuator-sensor module into the gas detecting data and outputs thereof, and wherein the microprocessor transmits the image data and the gas detecting data to the data transmitter, whereby the image data and the gas detecting data is transmitted to the cloud data processing device through the data transmitter for being stored and intelligently analyzed.

3. The monitoring and gas detection information notification system according to claim 1, wherein the data network is a wired network.

4. The monitoring and gas detection information notification system according to claim 1, wherein the data network is a wireless network.

5. The monitoring and gas detection information notification system according to claim 1, wherein the notification processing system starts an air quality notification processing mechanism device, wherein the air quality notification processing mechanism device transmits air quality notification information to a user device.

6. The monitoring and gas detection information notification system according to claim 1, wherein the actuator is a micro-electromechanical systems (MEMS) pump.

7. The monitoring and gas detection information notification system according to claim 6, wherein the micro-electromechanical systems pump comprises:
 a first substrate having a plurality of inlets, wherein each of the plurality of inlets is a conical hole;
 a first oxide layer stacked on the first substrate, wherein the first oxide layer has a plurality of convergence troughs and an oxide layer convergence chamber, wherein the plurality of convergence troughs is in communication between the oxide layer convergence chamber and the plurality of inlets;
 a second substrate combined with the first substrate, comprising:
 a silicon wafer layer, having:
 an actuation portion being circular;
 an outer peripheral portion being in a hollow ring shape and surrounding the periphery of the actuation portion;
 a plurality of connection portions respectively connected between the actuation portion and the outer peripheral portion; and
 a plurality of fluid channels surrounding the periphery of the actuation portion and located between the plurality of connection portions;
 a second oxide layer formed on the silicon wafer layer, wherein the second oxide layer is in a hollow ring shape, and the second oxide layer and the silicon wafer layer together define a vibration chamber;
 a silicon material layer being in a circular shape and located at the second oxide layer, wherein the silicon material layer is combined with the first oxide layer, and the silicon material layer has:
 a through hole located at a center portion of the silicon material layer;
 a vibration portion located at a peripheral area of the through hole; and
 a fixed portion located at a peripheral area of the silicon material layer; and
 a piezoelectric element being in a circular shape and stacked on the actuation portion of the silicon wafer layer.

8. The monitoring and gas detection information notification system according to claim 7, wherein the piezoelectric element comprises:
 a lower electrode layer;
 a piezoelectric layer stacked on the lower electrode layer;
 an insulation layer disposed on a part of a surface of the piezoelectric layer and a part of a surface of the lower electrode layer; and
 an upper electrode layer stacked on the insulation layer and a remaining portion of the surface of the piezoelectric layer where the insulation layer is not disposed, wherein the upper electrode layer is used for electrically connecting to the piezoelectric layer.

9. The monitoring and gas detection information notification system according to claim 1, wherein the actuator is a piezoelectric pump.

10. The monitoring and gas detection information notification system according to claim 9, wherein the piezoelectric pump comprises:
 an inlet plate having at least one inlet hole, at least one convergence channel, and a central recess forming a convergence chamber, wherein the at least one inlet hole is capable of guiding the gas outside the piezoelectric pump to flow therein, the at least one convergence channel corresponds to the at least one inlet hole, and the at least one convergence channel guides the gas from the at least one inlet hole to converge at the convergence chamber formed by the central recess;

a resonance sheet having a perforation corresponding to the convergence chamber, and a periphery of the perforation is a movable portion; and a piezoelectric actuator disposed correspondingly to the resonance sheet;

wherein a gap between the resonance sheet and the piezoelectric actuator forms a first chamber, so that when the piezoelectric actuator is driven, the gas is guided into the piezoelectric pump through the at least one inlet hole of the inlet plate, is converged at the central recess via the at least one convergence channel, flows through the perforation of the resonance sheet and then is transmitted to the first chamber by a resonance effect between the piezoelectric actuator and the movable portion of the resonance sheet.

11. The monitoring and gas detection information notification system according to claim 10, wherein the piezoelectric pump comprises:

a suspension plate having a first surface and a second surface, wherein the suspension plate is capable of bending and vibrating;

an outer frame disposed around a periphery of the suspension plate;

at least one supporting element connected between the suspension plate and the outer frame to provide a flexible support for the suspension plate; and a piezoelectric sheet having a side length, wherein the side length of the piezoelectric sheet is smaller than or equal to a side length of the suspension plate, and the piezoelectric sheet is attached to a first surface of the suspension plate so as to drive the suspension plate to bend and vibrate when the piezoelectric sheet is applied with a voltage.

12. The monitoring and gas detection information notification system according to claim 11, wherein the suspension plate is a square suspension plate, and the suspension plate has a protruding portion.

13. The monitoring and gas detection information notification system according to claim 10, wherein the piezoelectric pump comprises: a conductive sheet, a first insulation sheet, and a second insulation sheet, wherein the inlet plate, the resonance sheet, the first insulation sheet, the conductive sheet, the second insulation sheet are sequentially stacked and assembled with each other.

14. The monitoring and gas detection information notification system according to claim 9, wherein the piezoelectric pump comprises:

a nozzle plate comprising a suspension sheet and a hollow hole, wherein the suspension sheet is capable of bending and vibrating, and the hollow hole is formed at a central portion of the suspension sheet;

a chamber frame stacked on the suspension sheet;

an actuating body stacked on the chamber frame so as to bend and vibrate reciprocatingly when the actuating body is applied with a voltage;

an insulation frame stacked on the actuating body; and a conductive frame stacked on the insulation frame;

wherein the nozzle plate is fixed on four positioning bumps on a surface of the actuator-sensor module for being supported and positioned by the four positioning bumps, so that a spacing distance is defined between the nozzle plate and the surface of the actuator-sensor module for the gas to flow therethrough; a gas flow chamber is formed between the nozzle plate and the surface of the actuator-sensor module, and a resonance chamber is formed among the actuating body, the chamber frame, and the suspension sheet; wherein the nozzle plate is capable of being driven to move correspondingly by driving the actuating body, so that the suspension sheet of the nozzle plate vibrates vertically and reciprocatingly, and thus the gas enters into the gas flow chamber through the spacing distance and then is discharged out of the gas flow chamber, thereby achieving a transmission of gas flow.

15. The monitoring and gas detection information notification system according to claim 14, wherein the actuating body comprises:

a piezoelectric carrier plate stacked on the chamber frame;

an adjusting resonance plate stacked on the piezoelectric carrier plate; and a piezoelectric plate stacked on the adjusting resonance plate so as to drive the piezoelectric carrier plate and the adjusting resonance plate to bend and vibrate reciprocatingly when the piezoelectric plate is applied with a voltage.

16. The monitoring and gas detection information notification system according to claim 1, wherein the sensor comprises a gas sensor.

17. The monitoring and gas detection information notification system according to claim 1, wherein the sensor comprises a micro particle sensor.

18. The monitoring and gas detection information notification system according to claim 1, wherein the sensor comprises a volatile organic compounds (VOC) sensor.

* * * * *